United States Patent
Maruyama

(10) Patent No.: US 9,122,154 B2
(45) Date of Patent: Sep. 1, 2015

(54) RADIATION-SENSITIVE RESIN COMPOSITION, AND RADIATION-SENSITIVE ACID GENERATING AGENT

(71) Applicant: JSR CORPORATION, Tokyo (JP)

(72) Inventor: Ken Maruyama, Tokyo (JP)

(73) Assignee: JSR CORPORATION, Tokyo (JP)

( * ) Notice: Subject to any disclaimer, the term of this patent is extended or adjusted under 35 U.S.C. 154(b) by 3 days.

(21) Appl. No.: 13/937,048

(22) Filed: Jul. 8, 2013

(65) Prior Publication Data

US 2013/0295505 A1  Nov. 7, 2013
US 2014/0154625 A9  Jun. 5, 2014

Related U.S. Application Data

(63) Continuation of application No. PCT/JP2012/050290, filed on Jan. 10, 2012.

(30) Foreign Application Priority Data

Jan. 11, 2011 (JP) ................................. 2011-002627
Sep. 28, 2011 (JP) ................................. 2011-213584

(51) Int. Cl.

| | | |
|---|---|---|
| *G03F 7/004* | (2006.01) | |
| *C07C 309/06* | (2006.01) | |
| *C08K 5/42* | (2006.01) | |
| *C07C 309/12* | (2006.01) | |
| *C07C 381/12* | (2006.01) | |
| *C07D 493/08* | (2006.01) | |
| *G03F 7/039* | (2006.01) | |
| *G03F 7/20* | (2006.01) | |

(52) U.S. Cl.
CPC ............ *G03F 7/0045* (2013.01); *C07C 309/06* (2013.01); *C07C 309/12* (2013.01); *C07C 381/12* (2013.01); *C07D 493/08* (2013.01); *C08K 5/42* (2013.01); *G03F 7/0046* (2013.01); *G03F 7/0397* (2013.01); *G03F 7/2041* (2013.01)

(58) Field of Classification Search
CPC .. C07C 381/12; C07C 309/06; C07C 309/12; G03F 7/004; G03F 7/0046; G03F 7/0392; G03F 7/0397; G03F 7/2041
USPC ......... 430/270.1, 326, 910, 921, 925; 568/22, 568/24, 27, 28
See application file for complete search history.

(56) References Cited

U.S. PATENT DOCUMENTS

| | | | |
|---|---|---|---|
| 2007/0178405 A1* | 8/2007 | Kanda et al. ................ | 430/270.1 |
| 2009/0023095 A1* | 1/2009 | Hada et al. .................. | 430/281.1 |
| 2009/0104563 A1* | 4/2009 | Ishiduka et al. ............ | 430/285.1 |
| 2012/0082939 A1* | 4/2012 | Kawabata et al. ............ | 430/319 |

FOREIGN PATENT DOCUMENTS

| | | | |
|---|---|---|---|
| JP | 2002-145955 | | 5/2002 |
| JP | 2002-201232 | | 7/2002 |
| JP | 2002-363123 | | 12/2002 |
| JP | 2007-025240 | * | 2/2007 |
| JP | 2010-106236 | | 5/2010 |
| JP | 2010-155824 | | 7/2010 |
| JP | 2010-248174 | | 11/2010 |
| JP | 2010-276969 | | 12/2010 |
| JP | 2010-282189 | | 12/2010 |
| JP | 2012-78723 A | | 4/2012 |
| WO | WO 2008/047678 | | 4/2008 |
| WO | WO 2009/051088 | | 4/2009 |

OTHER PUBLICATIONS

Machine translation of JP 2007-025240, published on Feb. 1, 2007.*
International Search Report for corresponding International Application No. PCT/JP2012/050290, Feb. 14, 2012.
Office Action issued Oct. 7, 2014 in Japanese Patent Application No. 2012-552727 (with English language translation).

* cited by examiner

*Primary Examiner* — Anca Eoff
(74) *Attorney, Agent, or Firm* — Oblon, McClelland, Maier & Neustadt, L.L.P.

(57) ABSTRACT

A radiation-sensitive resin composition includes a compound represented by a formula (1), and a base polymer. In the formula (1), $R^1$ is a group represented by a formula (a1), and $M^+$ represents a radiation-degradable monovalent cation. In the formula (a1), $R^2$ represents a substituted or unsubstituted chain hydrocarbon group having 1 to 30 carbon atoms, or the like. $R^3$ represents a substituted or unsubstituted divalent hydrocarbon group having 1 to 30 carbon atoms, or the like. $R^{41}$ represents —CO—, or the like. $R^{42}$ represents —CO—, or the like. m is an integer of 0 to 2. n is an integer of 0 to 1. A site denoted by * is a binding site with —O— in the formula (1).

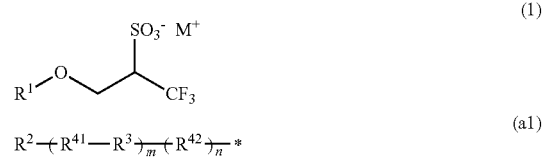

13 Claims, No Drawings

RADIATION-SENSITIVE RESIN COMPOSITION, AND RADIATION-SENSITIVE ACID GENERATING AGENT

CROSS-REFERENCE TO RELATED APPLICATIONS

The present application is a continuation application of International Application No. PCT/JP2012/050290, filed Jan. 10, 2012, which claims priority to Japanese Patent Application No. 2011-002627, filed Jan. 11, 2011, and to Japanese Patent Application No. 2011-213584, filed Sep. 28, 2011. The contents of these applications are incorporated herein by reference in their entirety.

BACKGROUND OF THE INVENTION

1. Field of the Invention

The present invention relates to a radiation-sensitive resin composition, and a radiation-sensitive acid generating agent.

2. Discussion of the Background

In the field of microfabrication, etc., typified by manufacturing of integrated circuit elements, lithography techniques have been recently required that enable microfabrication at a level of no greater than about 100 nm in order to achieve higher integrity. Examples of radioactive rays which may be used in such microfabrication include far ultraviolet rays such as a KrF excimer laser, an ArF excimer laser, an $F_2$ excimer laser and an EUV (extreme ultraviolet) ray, X-rays such as a synchrotron radioactive ray, charged particle rays such as an electron beam, and the like. As radiation-sensitive resin compositions suited for such a radioactive ray, a number of chemically amplified radiation-sensitive resin compositions have been proposed which contain a component having an acid-dissociable group and an acid generating agent which is a component that generates an acid by irradiation with a radioactive ray, and utilizes a chemical amplification effect between these components. Such a radiation-sensitive resin composition which has been known contains, for example, a polymer that includes a monomer unit having a norbornane ring derivative (see Japanese Unexamined Patent Application, Publication No. 2002-201232 and Japanese Unexamined Patent Application, Publication No. 2002-145955). Moreover, a radiation-sensitive resin composition containing in addition to a component having an acid-dissociable group and an acid generating agent, a photoactive compound further added in order to improve sensitivity and resolution has been also known (see Japanese Unexamined Patent Application, Publication No. 2002-363123).

Under such circumstances, demands for higher integrity in the field of semiconductors, etc., lead to a requirement for resist films having more balanced lithography performances. Particularly, a resist film that exhibits favorable resistance to pattern collapse after development, LWR (Line Width Roughness) and MEEF (Mask Error Enhancement Factor), which are well coordinated, has been strongly demanded.

SUMMARY OF THE INVENTION

According to one aspect of the present invention, a radiation-sensitive resin composition includes a compound represented by a formula (1), and a base polymer.

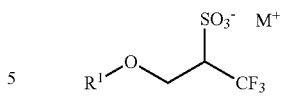

(1)

In the formula (1), $R^1$ is a group represented by a formula (a1); and $M^+$ represents a radiation-degradable monovalent cation.

(a1)

In the formula (a1), $R^2$ represents a chain hydrocarbon group having 1 to 30 carbon atoms, an alicyclic hydrocarbon group having 3 to 30 carbon atoms or a heterocyclic group having 3 to 30 ring atoms; $R^3$ represents a divalent hydrocarbon group having 1 to 30 carbon atoms, wherein a part or all of hydrogen atoms included in the chain hydrocarbon group, the alicyclic hydrocarbon group and the heterocyclic group represented by $R^2$, and a part or all of hydrogen atoms included in the hydrocarbon group represented by $R^3$ are not substituted or substituted; $R^{41}$ represents —CO—, —COO—, —OCO—, —O—CO—O—, —NHCO—, —CONH—, —NH—CO—O—, —O—CO—NH—, —NH—, —S—, —SO—, —$SO_2$— or —$SO_2$—O—; $R^{42}$ represents —CO—, —COO—, —OCO—, —NHCO—, —CONH—, —NH—CO—O—, —SO— or —$SO_2$—; m is an integer of 0 to 2; and n is an integer of 0 to 1, wherein in a case where $R^3$, $R^{41}$ and $R^{42}$ are each present in a plurality of number, a plurality of $R^3$s, $R^{41}$s or $R^{42}$s are each independently as defined, and wherein a site denoted by * is a binding site with —O— in the formula (1).

According to another aspect of the present invention, a radiation-sensitive acid generating agent includes a compound represented by a formula (1).

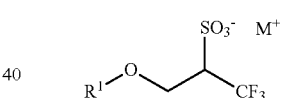

(1)

In the formula (1), $R^1$ is a group represented by a formula (a1); and $M^+$ represents a radiation-degradable monovalent cation.

(a1)

In the formula (a1), $R^2$ represents a chain hydrocarbon group having 1 to 30 carbon atoms, an alicyclic hydrocarbon group having 3 to 30 carbon atoms or a heterocyclic group having 3 to 30 ring atoms; $R^3$ represents a divalent hydrocarbon group having 1 to 30 carbon atoms, wherein a part or all of hydrogen atoms included in the chain hydrocarbon group, the alicyclic hydrocarbon group and the heterocyclic group represented by $R^2$, and a part or all of hydrogen atoms included in the hydrocarbon group represented by $R^3$ are not substituted or substituted; $R^{41}$ represents —CO—, —COO—, —OCO—, —O—CO—O—, —NHCO—, —CONH—, —NH—CO—O—, —O—CO—NH—, —NH—, —S—, —SO—, —$SO_2$— or —$SO_2$—O—; $R^{42}$ represents —CO—, —COO—, —OCO—, —NHCO—, —CONH—, —NH—CO—O—, —SO— or —$SO_2$—; m is an integer of 0 to 2; and n is an integer of 0 to 1, wherein in a case where $R^3$, $R^{41}$ and $R^{42}$ are each present in a plurality of number, a plurality of $R^3$s, $R^{41}$s or $R^{42}$s are each independently as defined, and wherein a site denoted by * is a binding site with —O— in the formula (1).

DESCRIPTION OF THE EMBODIMENTS

More specifically, a radiation-sensitive resin composition according to an embodiment of the present invention contains:

a compound represented by the following formula (1) (hereinafter, may be also referred to as "compound (A)"); and a base polymer, which is a polymer that serves as a base (hereinafter, may be also referred to as "polymer (B)"):

(1)

wherein, in the formula (1), $R^1$ represents a monovalent hydrocarbon group having 1 to 30 carbon atoms, wherein the hydrocarbon group may have —CO—, —COO—, —OCO—, —O—CO—O—, —NHCO—, —CONH—, —O—CO—NH—, —NH—, —S—, —SO—, —SO$_2$—, —SO$_2$—O— or a combination thereof within a bond between carbon atoms, and wherein a part or all of hydrogen atoms included in the hydrocarbon group are not substituted or substituted; and $M^+$ represents a radiation-degradable monovalent cation.

The radiation-sensitive resin composition is superior in transparency to radioactive rays due to the compound (A) having a specific structure used as an acid generating agent. Thus, according to the radiation-sensitive resin composition, a chemically amplified resist film can be provided upon a response to a radioactive ray or heating, the resist film being favorable in resistance to pattern collapse after development, LWR and MEEF, and superior in a coordination thereof.

$R^1$ in the above formula (1) is preferably a group represented by the following formula (a1):

(a1)

wherein, in the formula (a1), $R^2$ represents a chain hydrocarbon group having 1 to 30 carbon atoms, an alicyclic hydrocarbon group having 3 to 30 carbon atoms or a heterocyclic group having 3 to 30 ring atoms; $R^3$ represents a divalent hydrocarbon group having 1 to 30 carbon atoms, wherein a part or all of hydrogen atoms included in the chain hydrocarbon group, the alicyclic hydrocarbon group and the heterocyclic group represented by $R^2$, and a part or all of hydrogen atoms included in the hydrocarbon group represented by $R^3$ are not substituted or substituted; $R^{41}$ represents —CO—, —COO—, —OCO—, —O—CO—O—, —NHCO—, —CONH—, —NH—CO—O—, —O—CO—NH—, —NH—, —S—, —SO—, —SO$_2$— or —SO$_2$—O—; $R^{42}$ represents —CO—, —COO—, —OCO—, —NHCO—, —CONH—, —NH—CO—O—, —SO— or —SO$_2$—; m is an integer of 0 to 2; and n is an integer of 0 to 1, wherein in a case where $R^3$, $R^{41}$ and $R^{42}$ are each present in a plurality of number, a plurality of $R^3$s, $R^{41}$s or $R^{42}$s are each independently as defined above, and wherein a site denoted by * is a binding site with —O— in the above formula (1).

When the group represented by $R^1$ has the structure described above, resistance to pattern collapse after development, LWR and MEEF can be further improved.

$M^+$ in the above formula (1) preferably represents a sulfonium cation or an iodonium cation. The characteristics described above can be further improved by using such a cation.

The base polymer (B) preferably has a structural unit represented by the following formula (2):

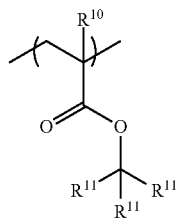
(2)

wherein, in the formula (2), $R^{10}$ represents a hydrogen atom or a methyl group; and $R^{11}$s each independently represent a linear or branched alkyl group having 1 to 4 carbon atoms or an alicyclic group having 4 to 20 carbon atoms, or two of $R^{11}$s taken together represent an alicyclic group having 4 to 20 carbon atoms together with the carbon atom to which the two of $R^{11}$s bond and $R^{11}$ other than the two of $R^{11}$s represents a linear or branched alkyl group having 1 to 4 carbon atoms or an alicyclic group having 4 to 20 carbon atoms.

When the base polymer (B) has the aforementioned structural unit, the characteristics described above can be further improved.

The radiation-sensitive acid generating agent of the embodiment of the present invention includes a compound represented by the following formula (1):

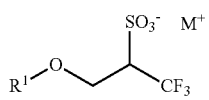
(1)

wherein, in the formula (1), $R^1$ represents a monovalent hydrocarbon group having 1 to 30 carbon atoms, wherein the hydrocarbon group does not include or includes —CO—, —COO—, —OCO—, —O—CO—O—, —NHCO—, —CONH—, —NH—CO—O—, —O—CO—NH—, —NH—, —S—, —SO—, —SO$_2$—, —SO$_2$—O— or a combination thereof within a bond between carbon atoms, and wherein a part or all of hydrogen atoms included in the hydrocarbon group are not substituted or substituted; and $M^+$ represents a radiation-degradable monovalent cation.

When the radiation-sensitive acid generating agent is used in a radiation-sensitive resin composition, a chemically amplified resist film can be formed which is favorable in resistance to pattern collapse after development, LWR and MEEF, and superior in coordination thereof.

$R^1$ in the above formula (1) is preferably a group represented by the following formula (a1):

(a1)

wherein, in the formula (a1), $R^2$ represents a chain hydrocarbon group having 1 to 30 carbon atoms, an alicyclic hydrocarbon group having 3 to 30 carbon atoms or a heterocyclic group having 3 to 30 ring atoms; $R^3$ represents a divalent hydrocarbon group having 1 to 30 carbon atoms, wherein a part or all of hydrogen atoms included in the chain hydrocarbon group, the alicyclic hydrocarbon group and the heterocyclic group represented by $R^2$, and a part or all of hydrogen atoms included in the hydrocarbon group represented by $R^3$ are not substituted or substituted; $R^{41}$ represents —CO—, —COO—, —OCO—, —O—CO—O—, —NHCO—, —CONH—, —NH—CO—O—, —O—CO—NH—, —NH—, —S—, —SO—, —SO$_2$— or —SO$_2$—O—; $R^{42}$ represents —CO—, —COO—, —OCO—, —NHCO—, —CONH—, —NH—CO—O—, —SO— or —SO$_2$—; m is an integer of 0 to 2; and n is an integer of 0 to 1, wherein in a case where $R^3$, $R^{41}$ and $R^{42}$ are each present in a plurality of number, a plurality of $R^3$s, $R^{41}$s or $R^{42}$s are each independently as defined above, and wherein a site denoted by * is a binding site with —O— in the above formula (1).)

When the compound included in the radiation-sensitive acid generating agent has such a structure, the characteristics described above can be more effectively achieved.

The radiation-sensitive resin composition of the embodiment of the present invention is capable of forming a resist film that is favorable in resistance to pattern collapse after development, LWR and MEEF, and superior in coordination thereof. In addition, when the radiation-sensitive acid generating agent of the embodiment of the present invention is used in a radiation-sensitive resin composition, a chemically amplified resist film can be formed which is favorable in resistance to pattern collapse after development, LWR and MEEF, and superior in coordination thereof.

Hereinafter, embodiments of the radiation-sensitive resin composition and the radiation-sensitive acid generating agent of the present invention will be explained. However, it should be construed that the present invention is not limited to the following embodiments, and any appropriate alterations, modifications and the like of the following embodiments made without departing from the spirit of the present invention, based on common knowledge that persons skilled in the art have may fall within the scope of the present invention.

Radiation-Sensitive Resin Composition

The radiation-sensitive resin composition of the embodiment of the present invention contains the compound (A) and the polymer (B). The radiation-sensitive resin composition preferably contains as favorable components, (C) a polymer that includes a fluorine atom (hereinafter, may be also referred to as "polymer (C)"), (D) an acid diffusion control agent and (E) a lactone compound, and may further contain other optional component(s).

(A) Compound

The compound (A) is represented by the above formula (1). The compound (A) generates a compound (acid) represented by $R^1$—O—CH$_2$—CH(CF$_3$)—SO$_3$H upon irradiation with a radioactive ray.

$R^1$ represents a monovalent hydrocarbon group having 1 to 30 carbon atoms, wherein the hydrocarbon group does not include or includes —CO—, —COO—, —OCO—, —O—CO—O—, —NHCO—, —CONH—, —NH—CO—O—, —O—CO—NH—, —NH—, —S—, —SO—, —SO$_2$—, —SO$_2$—O— or a combination thereof within a bond between carbon atoms, and wherein a part or all of hydrogen atoms included in the hydrocarbon group are not substituted or substituted; and M$^+$ represents a radiation-degradable monovalent cation.

The hydrocarbon group is exemplified by a chain hydrocarbon group, an alicyclic hydrocarbon group, an aromatic hydrocarbon group and the like, preferably a chain hydrocarbon group and an alicyclic hydrocarbon group, and more preferably an alicyclic hydrocarbon group. The alicyclic hydrocarbon group may be either monocyclic or polycyclic.

Examples of the substituent which may be included in the hydrocarbon group include a hydroxyl group, a carboxyl group, a carbonyl group, a nitro group, an amino group, a silyl group, a halogen atom, thienyl group, and the like.

$R^1$ is preferably a group represented by the above formula (a1).

In the formula (a1), $R^2$ represents a chain hydrocarbon group having 1 to 30 carbon atoms, an alicyclic hydrocarbon group having 3 to 30 carbon atoms or a heterocyclic group having 3 to 30 ring atoms; $R^3$ represents a divalent hydrocarbon group having 1 to 30 carbon atoms, wherein a part or all of hydrogen atoms included in the chain hydrocarbon group, the alicyclic hydrocarbon group and the heterocyclic group represented by $R^2$, and a part or all of hydrogen atoms included in the hydrocarbon group represented by $R^3$ are not substituted or substituted; $R^{41}$ represents —CO—, —COO—, —OCO—, —O—CO—O—, —NHCO—, —CONH—, —NH—CO—O—, —O—CO—NH—, —NH—, —S—, —SO—, —SO$_2$— or —SO$_2$—O—; $R^{42}$ represents —CO—, —COO—, —OCO—, —NHCO—, —CONH—, —NH—CO—O—, —SO— or —SO$_2$—; m is an integer of 0 to 2; and n is an integer of 0 to 1, wherein in a case where $R^3$, $R^{41}$ and $R^{42}$ are each present in a plurality of number, a plurality of $R^3$s, $R^{41}$s or $R^{42}$s are each independently as defined above, and wherein a site denoted by * is a binding site with —O— in the above formula (1).

Examples of the chain hydrocarbon group having 1 to 30 carbon atoms include a methyl group, an ethyl group, a 1-propyl group, a 2-propyl group, a 1-butyl group, a 2-butyl group, a 2-(2-methylpropyl) group, a 1-pentyl group, a 2-pentyl group, a 3-pentyl group, a 1-(2-methylbutyl) group, a 1-(3-methylbutyl) group, a 2-(2-methylbutyl) group, a 2-(3-methylbutyl) group, a neopentyl group, a 1-hexyl group, a 2-hexyl group, a 3-hexyl group, a 1-(2-methylpentyl) group, a 1-(3-methylpentyl) group, a 1-(4-methylpentyl) group, a 2-(2-methylpentyl) group, a 2-(3-methylpentyl) group, a 2-(4-methylpentyl) group, a 3-(2-methylpentyl) group, a 3-(3-methylpentyl) group, and the like.

Examples of the alicyclic hydrocarbon group having 3 to 30 carbon atoms include a cyclopentyl group, a cyclohexyl group, a cycloheptyl group, a 2-norbornyl group, a 1-adamantyl group, a 2-adamantyl group, and the like. Of these, an alicyclic hydrocarbon group having 4 to 16 carbon atoms is preferred, and a cyclohexyl group and an adamantyl group are more preferred.

Examples of the heterocyclic group having 3 to 30 ring atoms include those having: a lactone structure such as butyrolactone, valerolactone, cyclohexanelactone or norbornanelactone; a cyclic carbonate structure represented by the following formula (a-1), etc.; a cyclic ketone structure represented by any one of the following formulae (b-1) to (b-7) etc.; a cyclic sulfide structure represented by any one of the following formulae (c-1) to (c-4) etc.; a structure represented by the following formula (d-1), and the like. Of these, groups having a lactone structure are preferred.

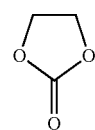

(a-1)

(b-1)

-continued

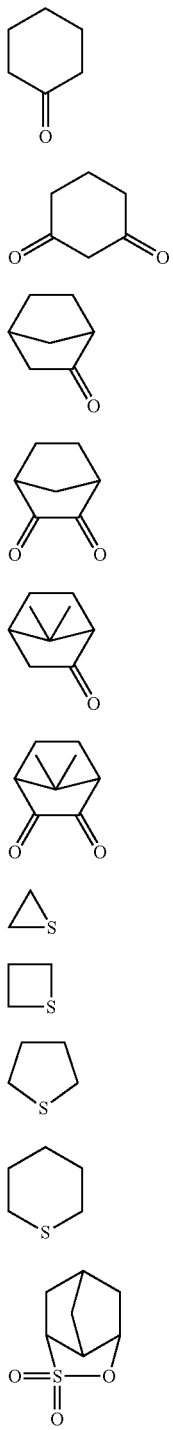

(b-2)
(b-3)
(b-4)
(b-5)
(b-6)
(b-7)
(c-1)
(c-2)
(c-3)
(c-4)
(d-1)

Examples of the substituent for the chain hydrocarbon group, the alicyclic hydrocarbon group and the heterocyclic group represented by $R^2$ include a hydroxyl group, a carboxyl group, a carbonyl group, a nitro group, an amino group, a silyl group, a halogen atom, a thienyl group, and the like.

$R^2$ preferably represents an alicyclic hydrocarbon group having 3 to 30 carbon atoms or a heterocyclic group having 3 to 30 ring atoms of the foregoing examples. Also, a group represented by the following formula (a2) is preferred.

(a2)

In the formula (a2), $R^{43}$ represents —CO—, —COO—, —OCO—, —O—CO—O—, —NHCO—, —CONH—, —NH—CO—O—, —O—CO—NH—, —NH—, —S—, —SO—, —SO$_2$— or —SO$_2$—O—; $R^5$ represents a divalent aliphatic hydrocarbon group having 1 to 30 carbon atoms, wherein a part or all of hydrogen atoms included in the aliphatic hydrocarbon group are not substituted or substituted; p is an integer of 0 to 3, wherein in a case where p is 0, Z represents a monovalent alicyclic hydrocarbon group having 1 to 30 carbon atoms, and in a case where p is an integer of 1 to 3, Z is a monovalent group that represents an aliphatic hetero ring structure taken together with —($R^{43}$—$R^5$)$_p$—, wherein in a case where $R^{43}$ and $R^5$ are each present in a plurality of number, the plurality of $R^{43}$s or $R^5$s are each independently as defined above.

Preferred examples of the divalent aliphatic hydrocarbon group represented by $R^5$ include groups having a structure derived by removing one hydrogen atom from the chain hydrocarbon group and the alicyclic hydrocarbon group described above. Examples of the substituent for the aliphatic hydrocarbon group include a hydroxyl group, a carboxyl group, a carbonyl group, a nitro group, an amino group, a silyl group, a halogen atom, a thienyl group, and the like.

In the above formula (a2), p is preferably 0 or 1. $R^{43}$ preferably represents —COO— or —OCO—. Z preferably represents an alicyclic hydrocarbon group having 4 to 16 carbon atoms or a group having a lactone structure.

Preferred examples of the divalent hydrocarbon group represented by $R^3$ include groups having a structure derived by removing one hydrogen atom from the chain hydrocarbon group and the alicyclic hydrocarbon group. Of these, an aliphatic hydrocarbon group having 1 to 30 carbon atoms is preferred, an aliphatic hydrocarbon group having 1 to 20 carbon atoms is more preferred, and an alicyclic hydrocarbon group having 4 to 10 carbon atoms is particularly preferred.

Examples of the substituent for the hydrocarbon group represented by $R^3$ include a hydroxyl group, a carboxyl group, a carbonyl group, a nitro group, an amino group, a silyl group, a halogen atom, a thienyl group, and the like.

In the above formula (a1), $R^2$ is preferably a group represented by the formula (a2) as described above. m is preferably 0 or 1. n is preferably 1. $R^{41}$ preferably represents —OCO—. $R^{42}$ preferably represents —CO—. When the compound has such a structure, the effects of the embodiment of the present invention can be more sufficiently achieved.

$M^+$ in the above formula (1) represents a radiation-degradable monovalent cation. $M^+$ preferably represents a sulfonium cation or an iodonium cation. When such a cation is used, the aforementioned characteristics can be further improved. In the case in which $M^+$ represents a sulfonium cation, the compound (A) is a sulfonium salt, and in the case in which $M^+$ represents an iodonium cation, the compound (A) is an iodonium salt.

Sulfonium Salt

The sulfonium salt is preferably represented by the following formula (4).

(4)

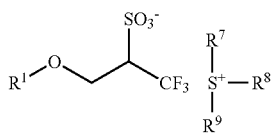

In the formula (4), $R^1$ is as defined in the above formula (1); $R^7$, $R^8$ and $R^9$ each independently represent a substituted or unsubstituted linear or branched alkyl group, alkenyl group or oxoalkyl group having 1 to 10 carbon atoms, or a substituted or unsubstituted aryl group, aralkyl group or aryloxoalkyl group having 6 to 18 carbon atoms. Wherein, any two or more of $R^7$, $R^8$ and $R^9$ may taken together represent a ring together with a sulfur atom in the formula.

Preferred examples of the sulfonium cation represented by the formula (4) include those represented by the following general formulae (4-1) and (4-2).

(4-1)

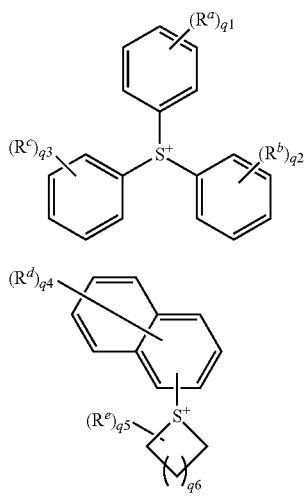

(4-2)

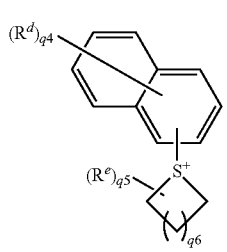

In the formula (4-1), $R^a$ to $R^c$ each independently represent a hydroxy group or a halogen atom, or an alkyl group, cycloalkyl group or alkoxy group which may have a substituent, an —S—R group (wherein R represents an alkyl group or aryl group which may have a substituent), or —SO$_2$—R' group (wherein R' represents an alkyl group, cycloalkyl group, alkoxy group or aryl group which may have a substituent); q1 to q3 are each independently an integer of 0 to 5, and in a case where $R^a$ to $R^c$ are each present in a plurality of number, the plurality of $R^a$s are each identical or different, the plurality of $R^b$s are each identical or different and the plurality of $R^c$s are each identical or different.

In the formula (4-2), $R^d$s which may be present in a plurality of number are each identical or different and $R^e$s present in a plurality of number are each identical or different, and $R^d$ represents a hydrogen atom, a substituted or unsubstituted linear or branched alkyl group having 1 to 8 carbon atoms, or a substituted or unsubstituted aryl group having 6 to 8 carbon atoms, wherein two or more of $R^d$s may taken together represent a ring; $R^e$ represents a hydrogen atom, a substituted or unsubstituted linear or branched alkyl group having 1 to 7 carbon atoms, or a substituted or unsubstituted aryl group having 6 to 7 carbon atoms, wherein two or more of $R^e$s may taken together represent a ring; $q^4$ is an integer of 0 to 7; $q^5$ is an integer of 0 to 6; and $q^6$ is an integer of 0 to 3.

Specific examples of the sulfonium cation include those represented by the following formulae (i-1) to (i-67).

(i-1)

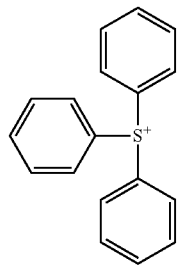

(i-2)

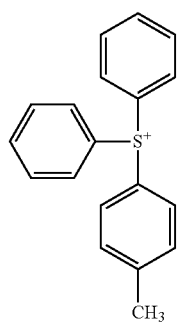

(i-3)

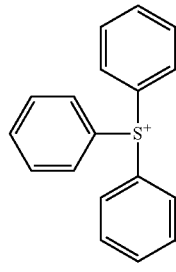

(i-4)

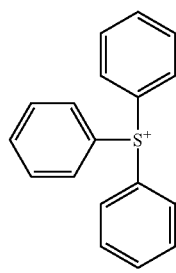

(i-5)

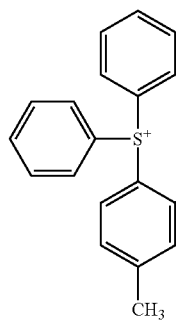

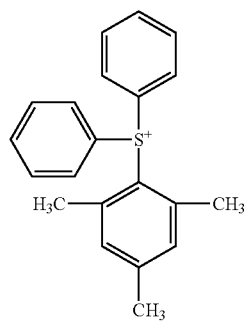
(i-6)
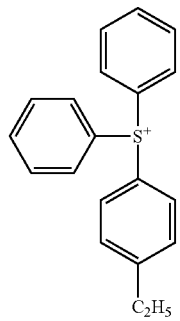
(i-10)
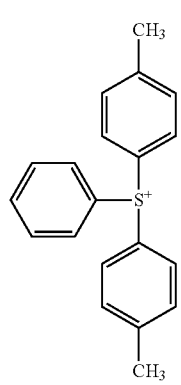
(i-7)
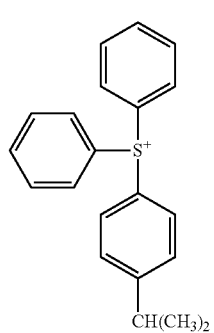
(i-11)
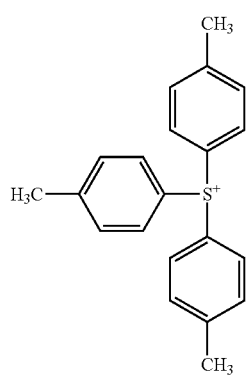
(i-8)
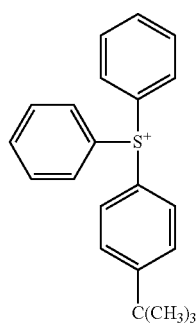
(i-12)
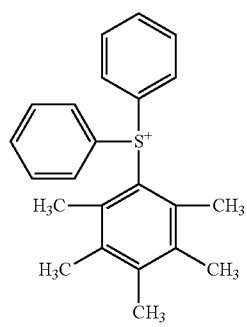
(i-9)
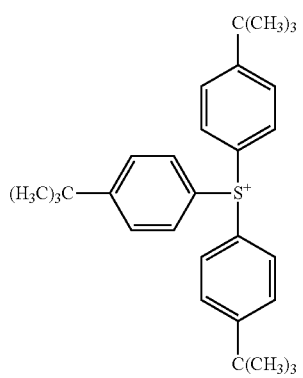
(i-13)

(i-14)
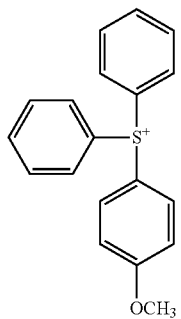
(i-15)
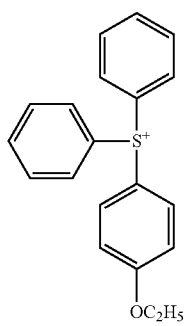
(i-16)
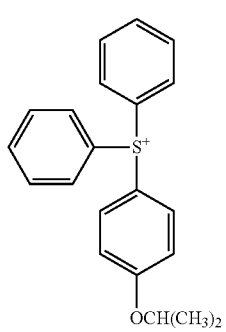
(i-17)
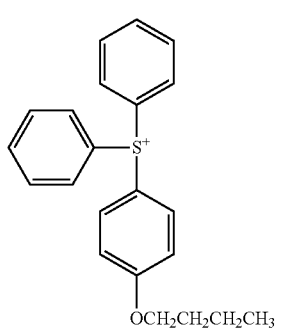
(i-18)
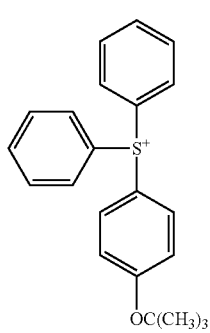
(i-19)
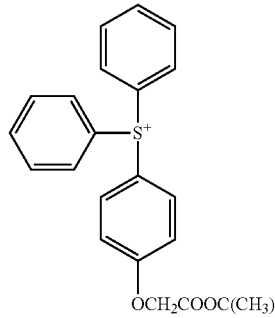
(i-20)
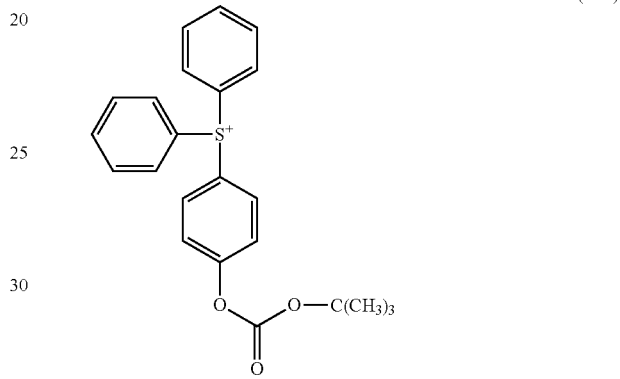
(i-21)
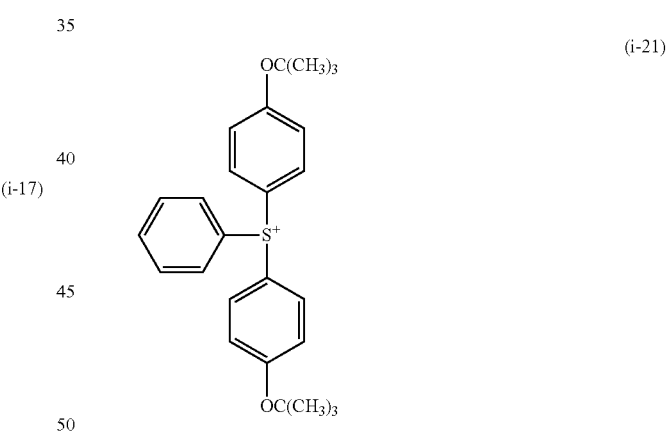
(i-22)
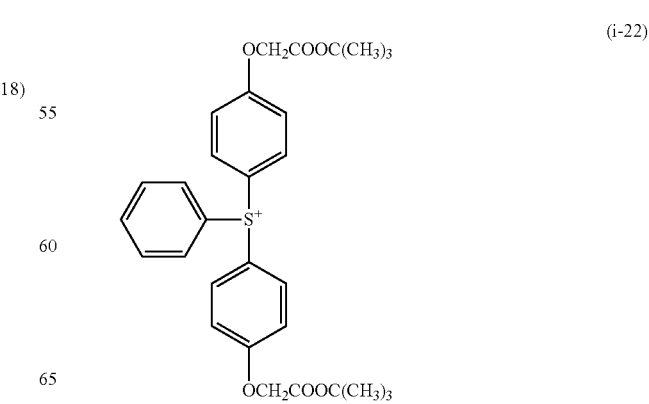

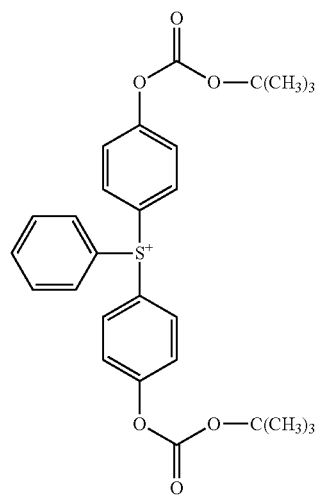
(i-23)
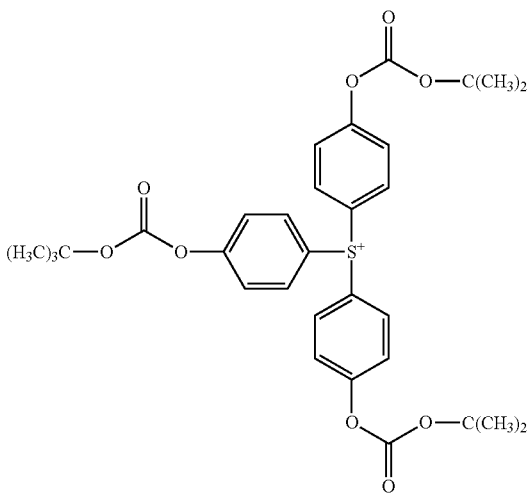
(i-26)
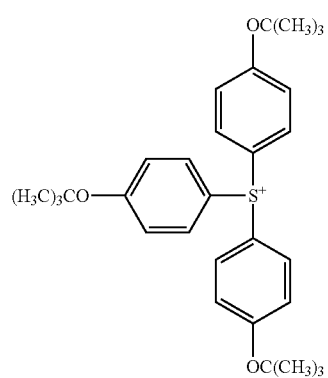
(i-24)
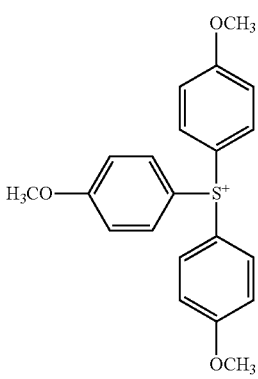
(i-27)
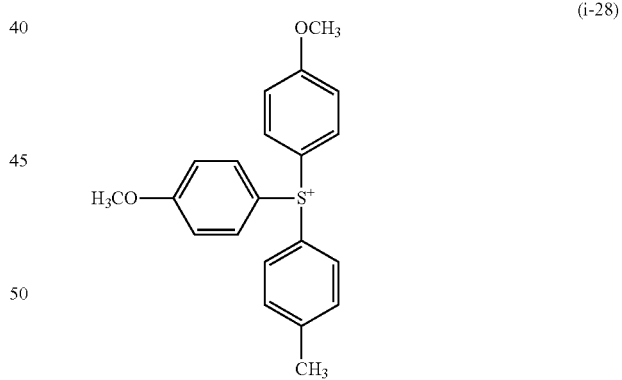
(i-28)
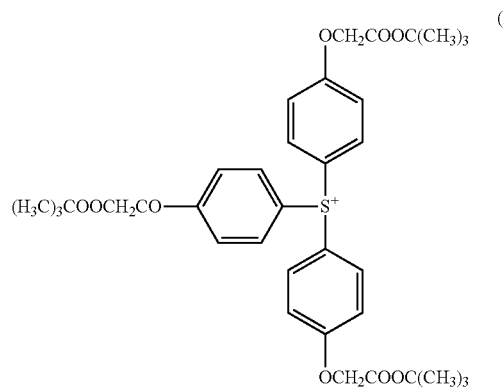
(i-25)
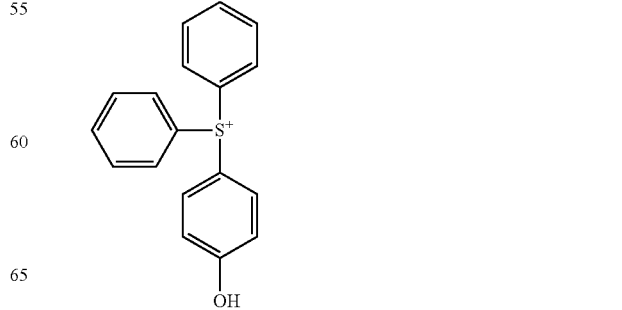
(i-29)

(i-30)
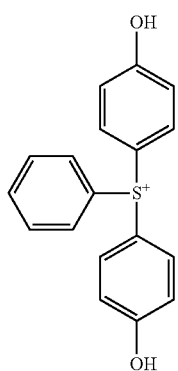
(i-31)
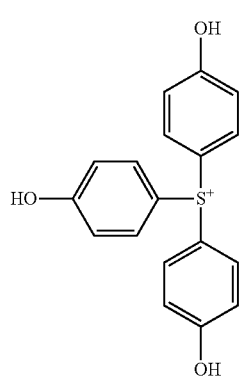
(i-32)
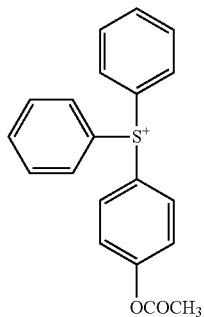
(i-33)
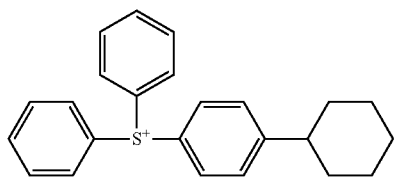
(i-34)
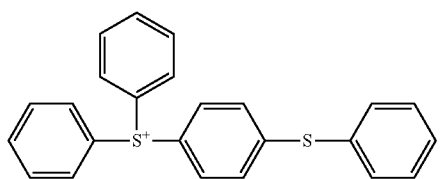
(i-35)
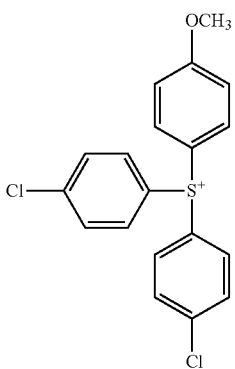
(i-36)
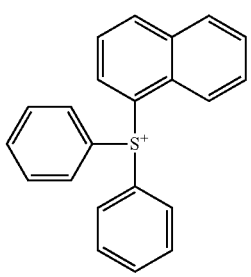
(i-37)
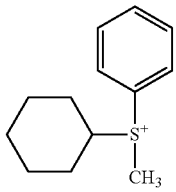
(i-38)
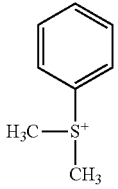
(i-39)
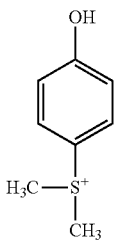
(i-40)
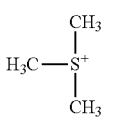
(i-41)

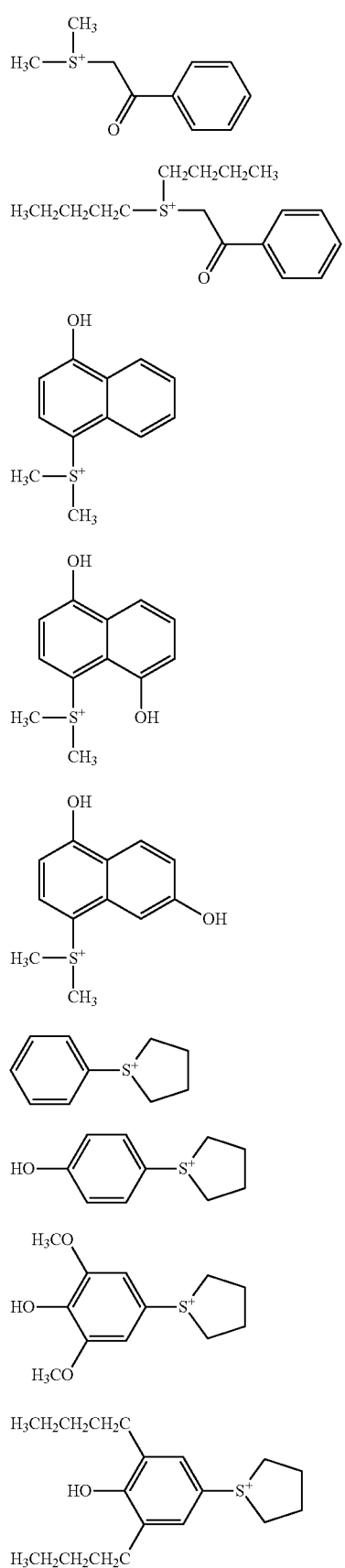
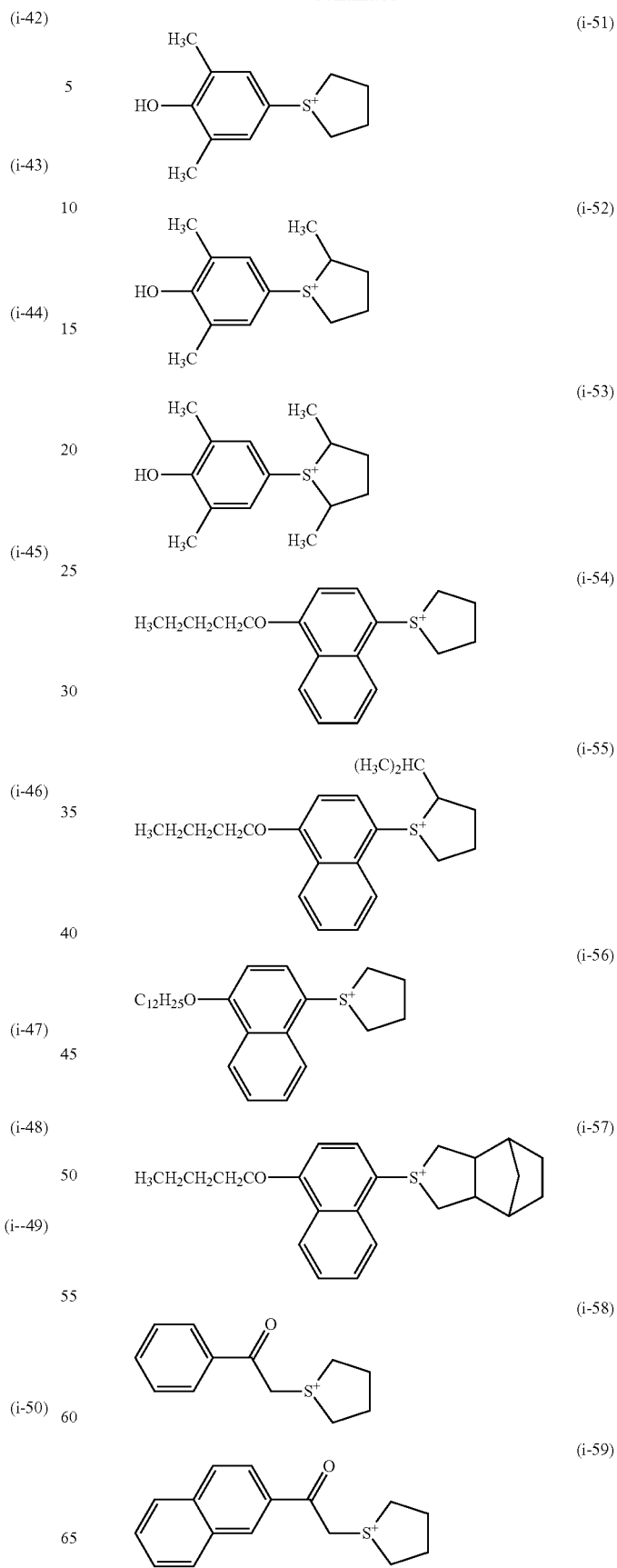

(i-60)
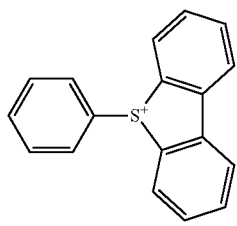

(i-61)
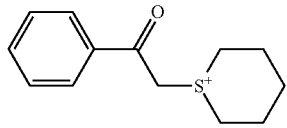

(i-62)
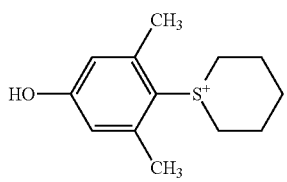

(i-63)
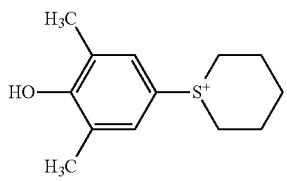

(i-64)
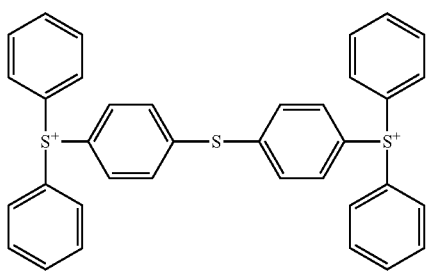

(i-65)
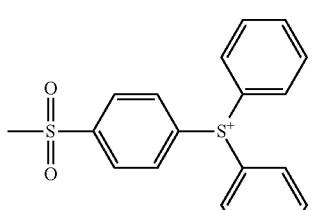

(i-66)
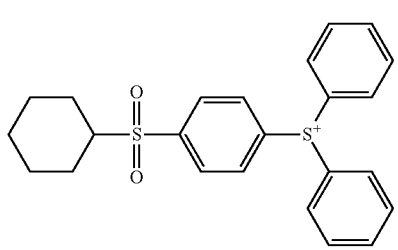

(i-67)
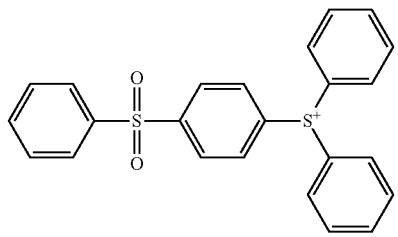

Iodonium Salt

The iodonium salt is preferably represented by the following formula (5).

(5)
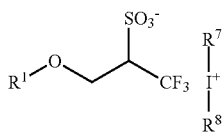

In the formula (5), $R^1$ is as defined in the above general formula (1); and $R^7$ and $R^8$ are as defined in the above formula (4).

Preferred examples of the iodonium cation represented by the above formula (5) include those represented by the following formula (5-1).

(5-1)
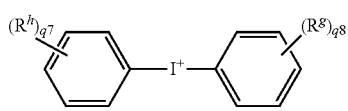

In the above formula (5-1), $R^h$s present in a plurality of number are each identical or different and $R^g$s present in a plurality of number are each identical or different, and $R^h$ and $R^g$ each represent a hydrogen atom, a substituted or unsubstituted linear or branched alkyl group having 1 to 12 carbon atoms, or a substituted or unsubstituted aryl group having 6 to 12 carbon atoms, wherein two or more of $R^f$s and $R^g$s may taken together represent a ring; and q7 and q8 are each independently an integer of 0 to 5.

Examples of the iodonium cation represented by the above formula (5-1) include those represented by the following formulae (ii1) to (ii-39).

(ii-1)
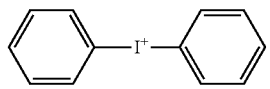

(ii-2)
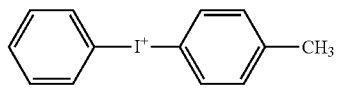

(ii-3)
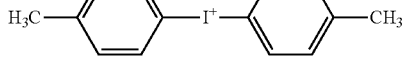

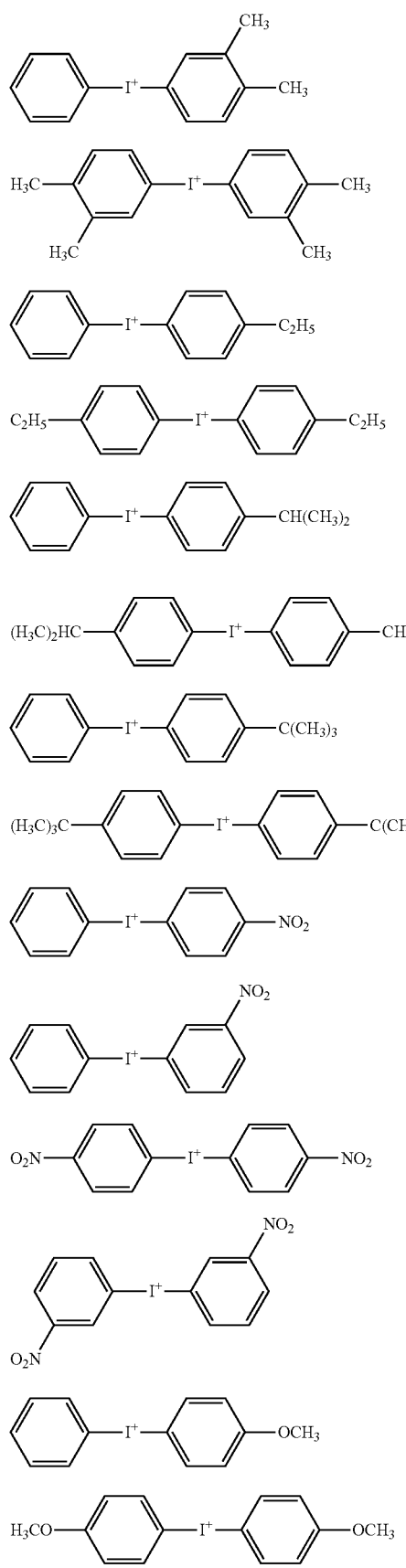
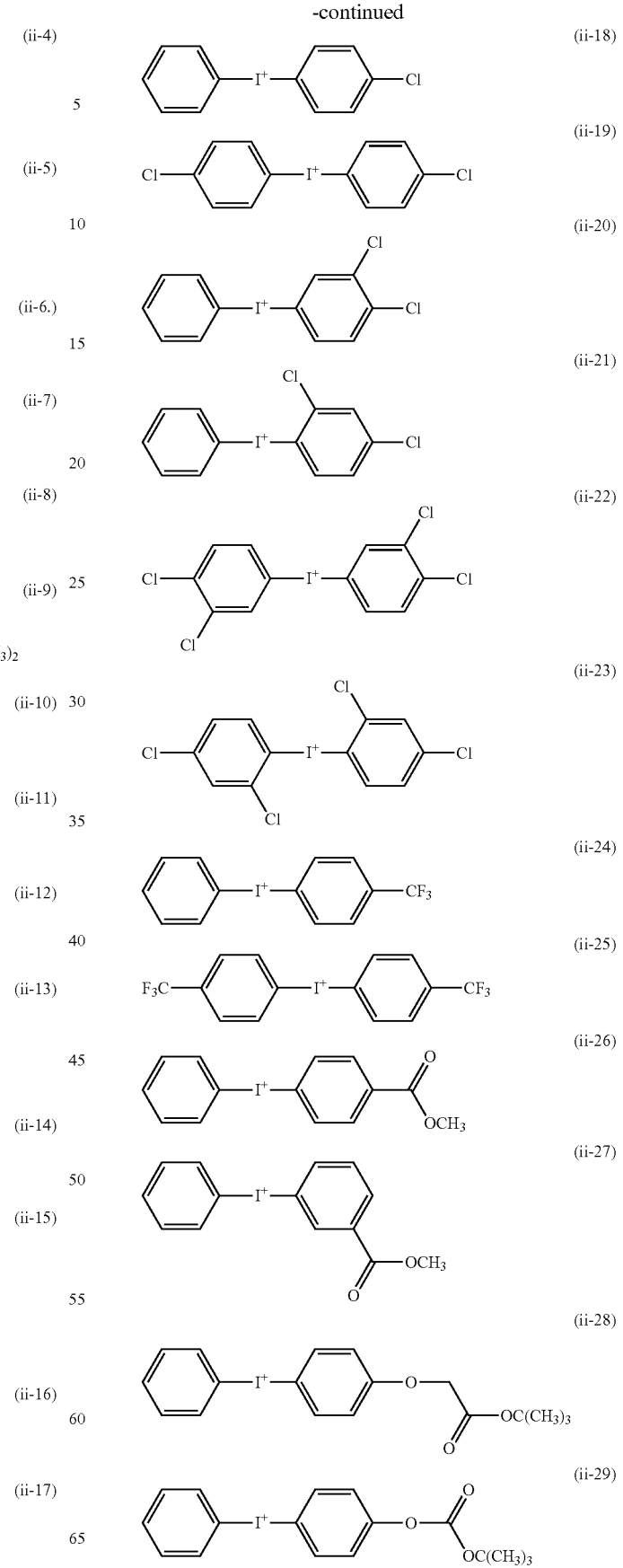

(ii-30) 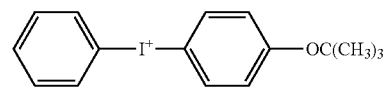

(ii-31) 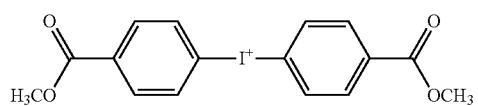

(ii-32) 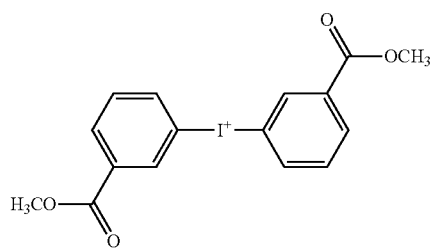

(ii-33) 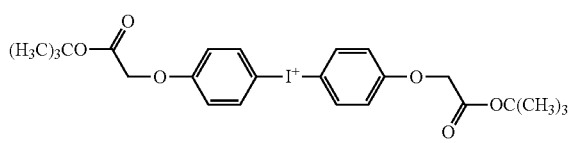

(ii-34) 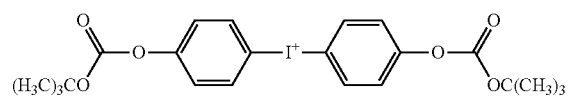

(ii-35) 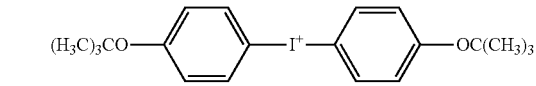

(ii-36) 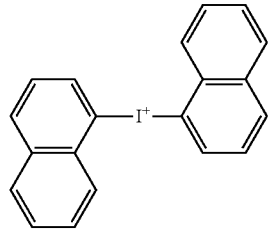

(ii-37) 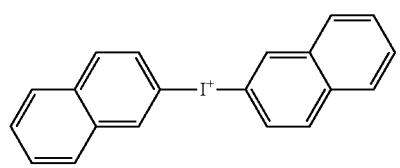

(ii-38) 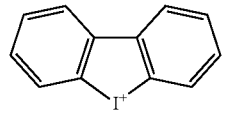

(ii-39) 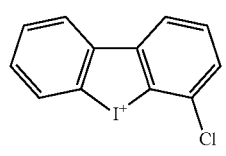

Among these cations represented by M⁺, sulfonium cations are more preferred, and cations represented by the above formula (4-1) are more preferred. Still further, cations represented by the above formula (4-1), wherein $q^1$ to $q^3$ are each independently 0 or 1 are preferred, and the cation represented by the above formula (i-1) or (i-67) is more preferred.

Preferred structures of the compound (A) are shown below.

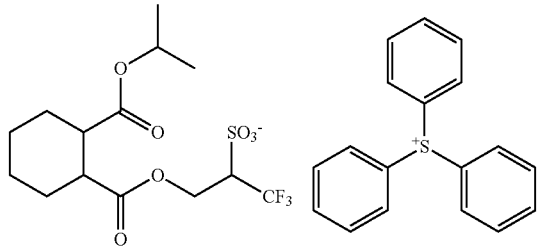

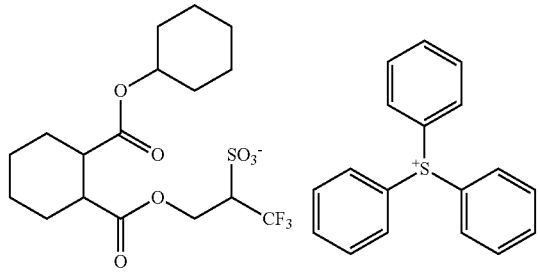

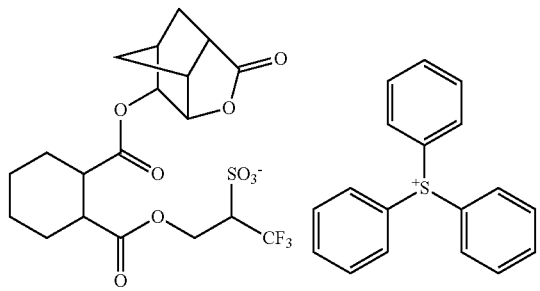

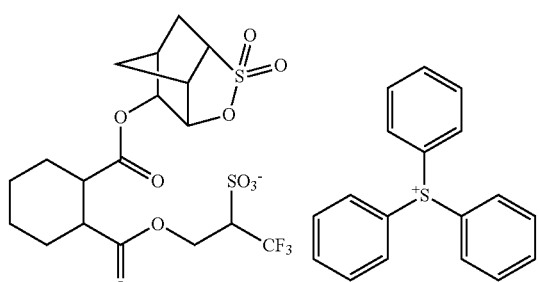

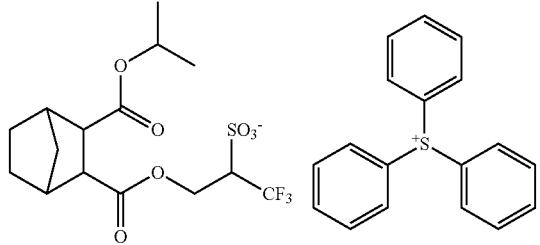

27
-continued
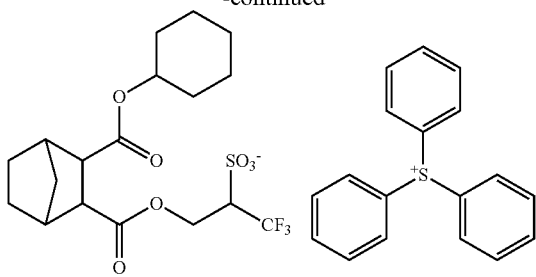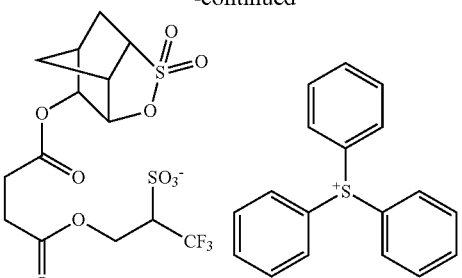
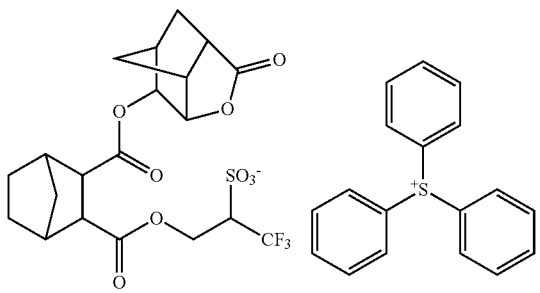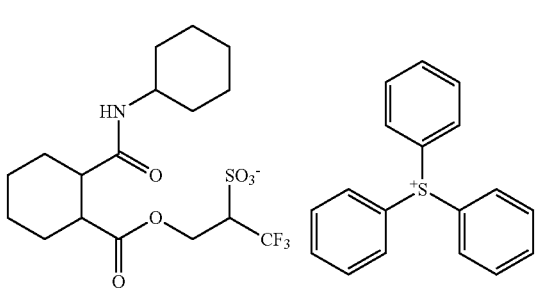
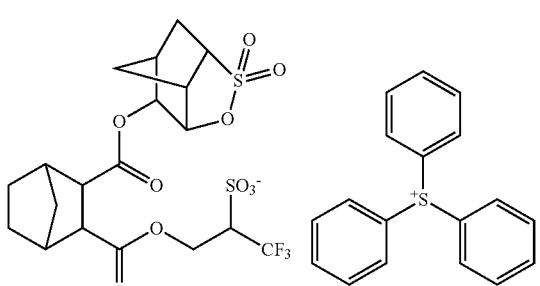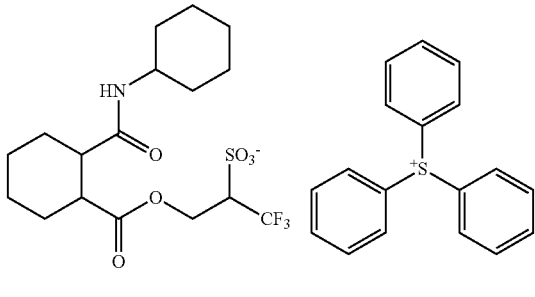
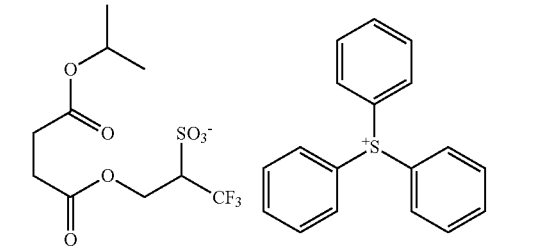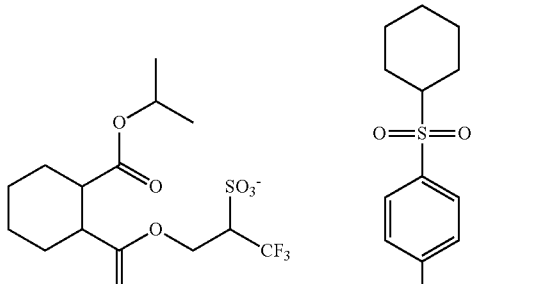
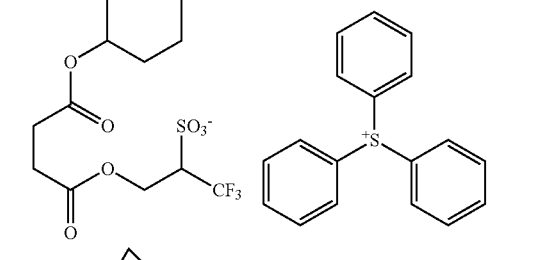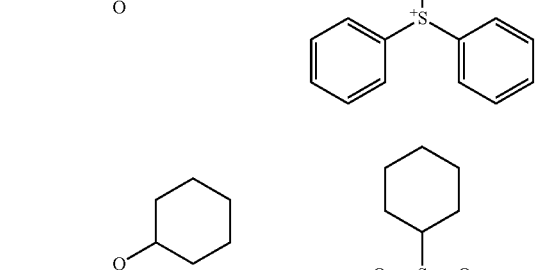
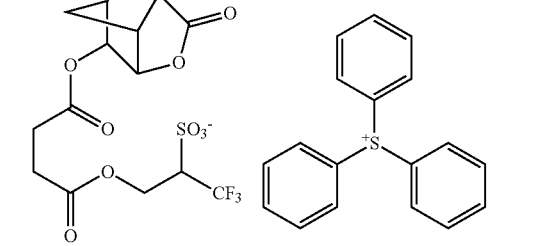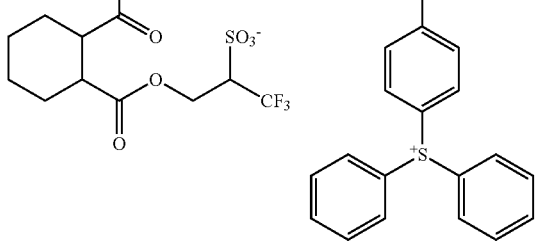
28
-continued

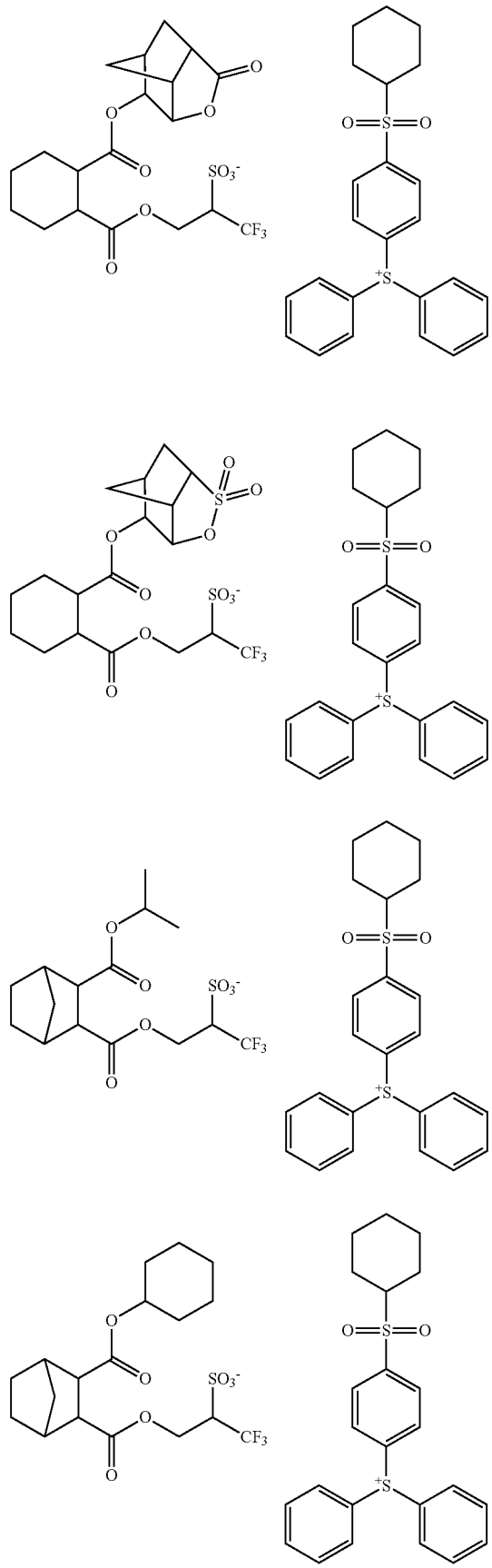
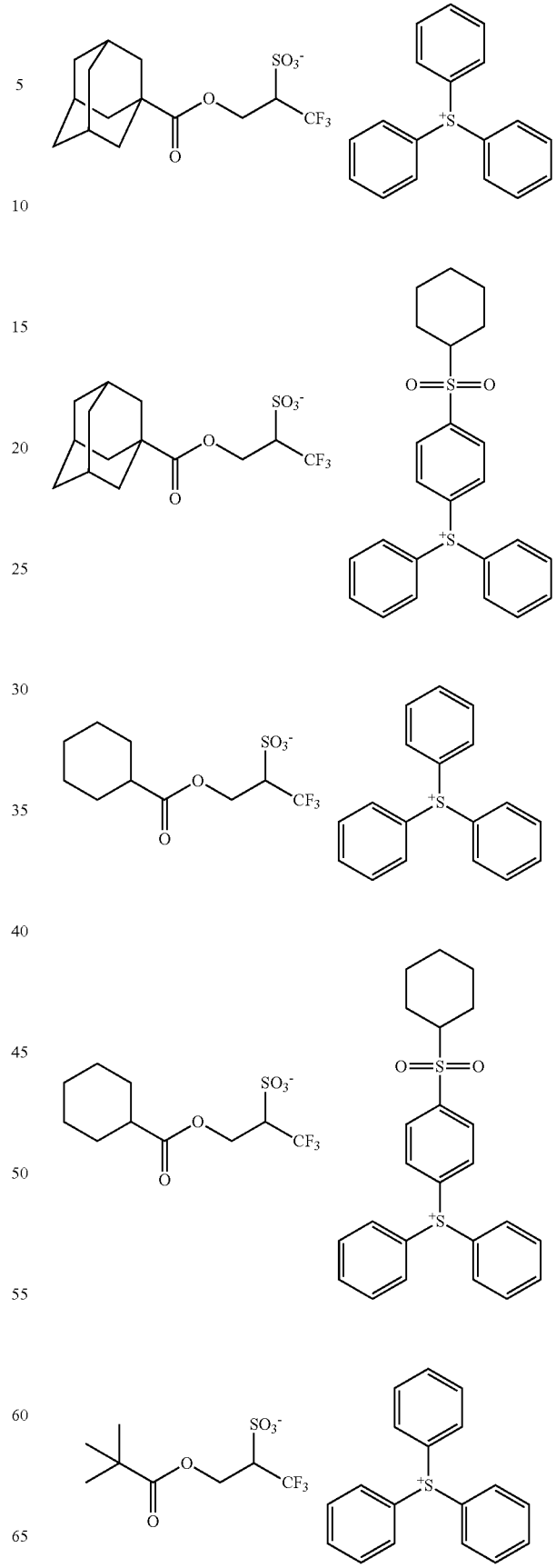

-continued

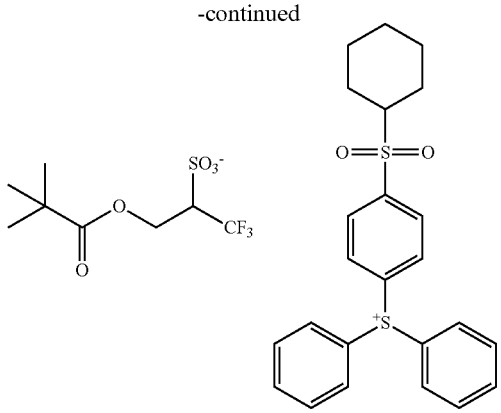

Synthesis Method of Compound (A)

The compound (A) in the embodiment of the present invention may be obtained according to, for example, a reaction shown by the following formula.

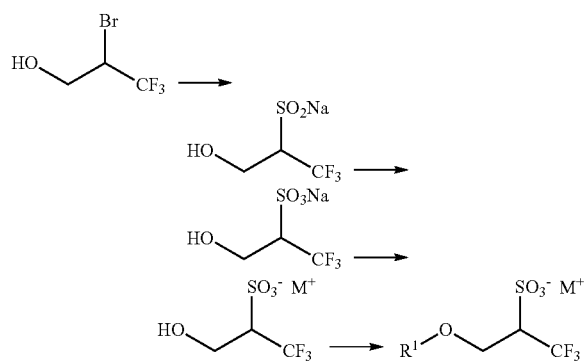

In the radiation-sensitive resin composition of the embodiment of the present invention, the compound (A) may be used either alone or as a mixture of two or more thereof.

In the radiation-sensitive resin composition of the embodiment of the present invention, the amount of the compound (A) used may vary depending on the type of the compound (A) and/or the type of the following other radiation-sensitive compound which may be used occasionally, and is typically 0.1 to 40 parts by mass, preferably 5 to 40 parts by mass, and more preferably 5 to 35 parts by mass with respect to 100 parts by mass of the polymer (B) described later. In this case, when the amount of the compound (A) is too small, desired effects of the embodiment of the present invention may not be satisfactorily exhibited, whereas an excessively high content may lead to deterioration of transparency against radioactive rays, pattern configuration, heat resistance and the like.

(B) Polymer

The polymer (B) serves as a base resin of the radiation-sensitive resin composition. In other words, the polymer (B) will be a principal component of a resist film formed from the radiation-sensitive resin. The amount of the polymer (B) contained in the solid content of the radiation-sensitive resin composition is preferably no less than 50% by mass, and more preferably no less than 70% by mass. As such a base polymer, for example, a polymer which is insoluble or hardly soluble in an alkali and has an acid-labile group and which becomes easily soluble in alkali when the acid-labile group dissociates (hereinafter, may be also referred to as "(B1) acid-labile group-containing polymer" or "(B1) polymer"), as well as a polymer that is soluble in an alkaline developer solution and that has a functional group having an affinity to the alkaline developer solution such as, for example, one or more types of oxygen-containing functional groups such as a phenolic hydroxyl group, an alcoholic hydroxyl group and a carboxyl group (hereinafter, may be also referred to as "(B2) alkali-soluble polymer" or "(B2) polymer") may be included. The radiation-sensitive resin composition containing the polymer (B1) can be suitably used as a positive radiation-sensitive resin composition, and the radiation-sensitive resin composition containing the polymer (B2) can be suitably used as a negative radiation-sensitive resin composition.

The term "insoluble or hardly soluble in alkali" as referred to herein means a property that no less than 50% of the initial film thickness of a coating remains after development in the case where the coating formed using only the polymer containing an acid-labile group is developed in place of the resist coating film under alkali development conditions employed in forming a resist pattern from a resist coating film formed using a radiation-sensitive resin composition that contains the polymer containing an acid-labile group.

When the polymer (C) described later is used, the proportion of the fluorine atom(s) included in the polymer (B) is typically less than 5% by mass, preferably 0 to 4.9% by mass, and more preferably 0 to 4% by mass. It is to be noted that the proportion of the fluorine atom(s) included can be determined by $^{13}$C-NMR. When the proportion of the fluorine atom(s) included in the polymer (B) falls within the above range, water repellency of the surface of the photoresist film formed with the composition containing the polymer (B) and the polymer (C) can be improved, and necessity of separately forming the upper layer film in liquid immersion lithography is obviated.

(B1) Acid-Labile Group-Containing Polymer

The acid-labile group in the acid-labile group-containing polymer (B 1) is a group derived by substituting a hydrogen atom in an acidic functional group such as a phenolic hydroxyl group, a carboxyl group or a sulfonic acid group, and means a group that is dissociated in the presence of an acid. Examples of such an acid-labile group include a substituted methyl group, a 1-substituted ethyl group, a 1-substituted n-propyl group, a 1-branched alkyl group, an alkoxycarbonyl group, an acyl group, a cyclic acid-labile group, and the like.

Examples of the substituted methyl group include those described in paragraph [0117] of WO2009/051088. In addition, examples of the 1-substituted ethyl group include those described in paragraph [0118] of WO2009/051088. Further, examples of the 1-substituted n-propyl group include those described in paragraph [0119] of WO2009/051088. Moreover, examples of the acyl group include those described in paragraph [0120] of WO2009/051088. Additionally, examples of the cyclic acid-labile group include those described in paragraph [0121] of WO2009/051088.

Among these acid-labile groups, a benzyl group, a t-butoxycarbonylmethyl group, a 1-methoxyethyl group, a 1-ethoxyethyl group, a 1-cyclohexyloxyethyl group, a 1-ethoxy-n-propyl group, a t-butyl group, a 1,1-dimethylpropyl group, a t-butoxycarbonyl group, a tetrahydropyranyl group, a tetrahydrofuranyl group, a tetrahydrothiopyranyl group, a tetrahydrothiofuranyl group and the like are preferred. In the acid-labile group-containing polymer, one or more types of the acid-labile groups may be present.

A percentage of introduction of the acid-labile group in the acid-labile group-containing polymer (a proportion of the number of the acid-labile group with respect to the total number of the acidic functional group and the acid-labile group in the acid-labile group-containing polymer) may be appropriately predetermined according to the type of the acid-labile group or the polymer to which the group is introduced, and is preferably 5 to 100% more preferably 10 to 100%.

In addition, the structure of the acid-labile group-containing polymer is not particularly limited as long as it has the features described above, and a variety of structures are acceptable, which may be particularly preferably a polymer derived from poly(4-hydroxystyrene) by substituting a part or all of hydrogen atoms in phenolic hydroxyl groups for the acid-labile group, a polymer derived from a copolymer of 4-hydroxystyrene and/or 4-hydroxy-α-methylstyrene with (meth)acrylic acid by substituting a part or all of hydrogen atoms in phenolic hydroxyl groups, and/or part or all of hydrogen atoms in carboxyl groups for the acid-labile group, and the like.

Structural Unit (10)

In addition, the structure of the acid-labile group-containing polymer may be variously selected in accordance with the type of the radioactive ray employed. For example, as the acid-labile group-containing polymer (B1) particularly suited for the positive radiation-sensitive resin composition for which a KrF excimer laser is employed, for example, a polymer that is insoluble or hardly soluble in alkali and that has a structural unit represented by the following formula (10) (hereinafter, may be referred to as "structural unit (10)") and a structural unit derived by protecting a phenolic hydroxyl group in the structural unit (10) with the acid-labile group is preferred. It is to be noted that the polymer may be suitably used for a positive radiation-sensitive resin composition for which other radioactive ray such as an ArF excimer laser, an F2 excimer laser or an electron beam is employed.

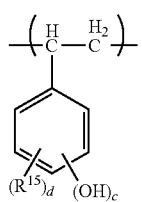

(10)

In the above formula (10), $R^{15}$ represents a hydrogen atom or a monovalent organic group, wherein $R^{15}$s present in a plurality of number may be each identical or different; and c and d are each an integer of 1 to 3.

The structural unit (10) is particularly preferably a unit derived by cleaving a nonaromatic double bond of 4-hydroxystyrene. In addition, the polymer may further include other structural unit.

Structural Unit (2)

Additionally, as the polymer (B) particularly suited for use in the positive radiation-sensitive resin composition for which an ArF excimer laser is employed preferably includes the structural unit represented by the above formula (2) (hereinafter, may be referred to as "structural unit (2)"). It is to be noted that the polymer (B) including the structural unit (2) may be suitably used also for a positive radiation-sensitive resin composition for which other radioactive ray such as a KrF excimer laser, an F2 excimer laser or an electron beam is employed.

In the formula (2), $R^{10}$ represents a hydrogen atom or a methyl group; and $R^{11}$s each independently represent a linear or branched alkyl group having 1 to 4 carbon atoms or an alicyclic group having 4 to 20 carbon atoms, or two of $R^{11}$s taken together represent an alicyclic group having 4 to 20 carbon atoms together with the carbon atom to which the two of $R^{11}$s bond and $R^{11}$ other than the two of $R^{11}$s represents a linear or branched alkyl group having 1 to 4 carbon atoms or an alicyclic group having 4 to 20 carbon atoms.

Examples of the alkyl group having 1 to 4 carbon atoms represented by $R^{11}$ in the above formula (2) include a methyl group, an ethyl group, a n-propyl group, a n-butyl group and the like, and examples of the monovalent alicyclic hydrocarbon group having 4 to 20 carbon atoms represented by $R^{11}$, or the divalent alicyclic hydrocarbon group having 4 to 20 carbon atoms taken together represented by two $R^{11}$s together with the carbon atom to which they bond include examples of the alicyclic hydrocarbon groups represented by $R^2$ described above.

The structural unit (2) is preferably a structural unit represented by any one of the following formulae (2-1) to (2-18), and particularly preferably a structural unit represented by any one of the following formulae (2-3), (2-4), (2-9), (2-12) and (2-13). These may be used either of one type alone, or two or more types thereof may be included.

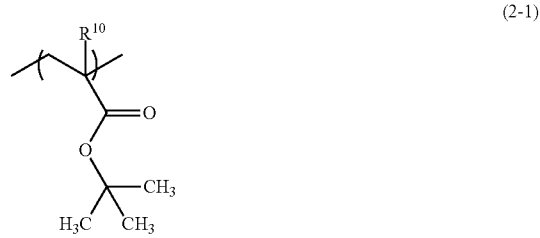

(2-1)

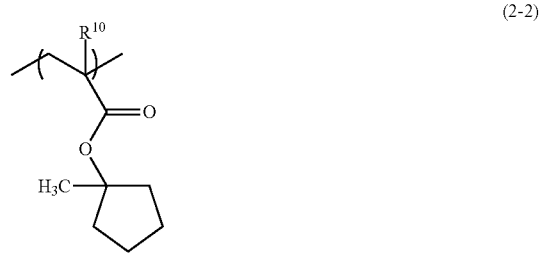

(2-2)

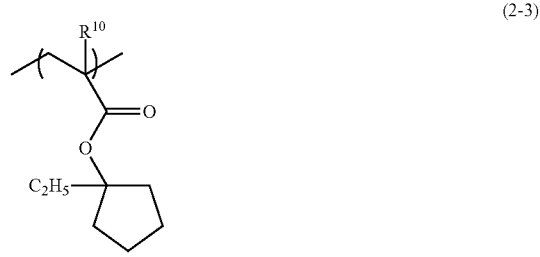

(2-3)

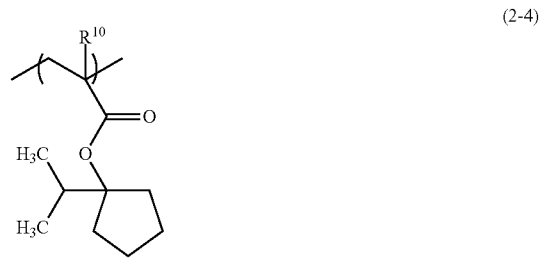

(2-4)

(2-5) 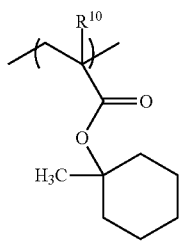
(2-6) 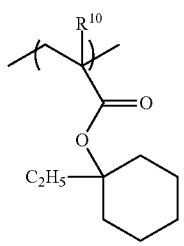
(2-7) 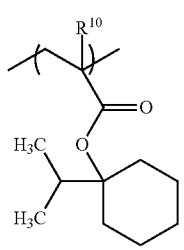
(2-8) 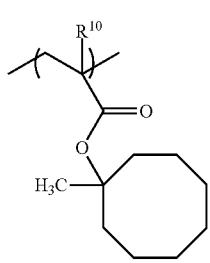
(2-9) 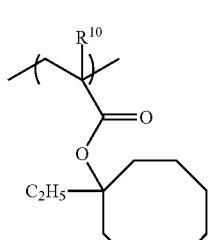
(2-10) 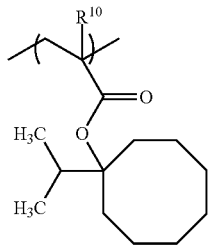
(2-11) 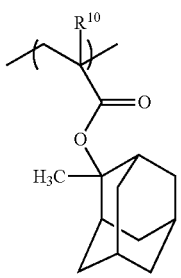
(2-12) 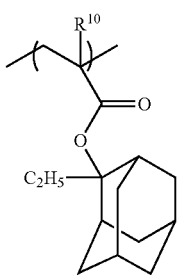
(2-13) 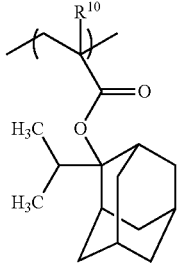
(2-14) 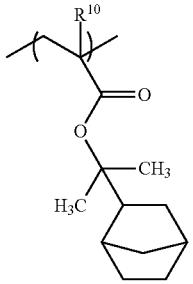
(2-15) 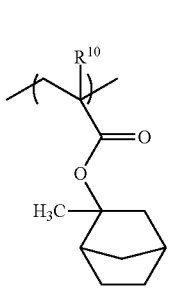

-continued

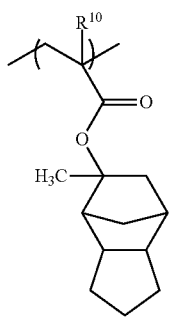
(2-16)

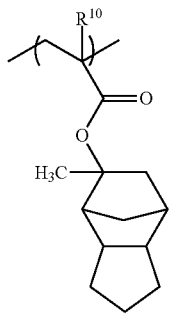
(2-17)

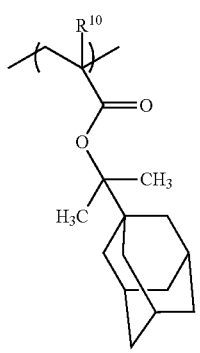
(2-18)

In the formulae, $R^{10}$ is as defined in the above formula (2).

The content of the structural unit (2) in the polymer (B) is preferably 20 to 70 mol %, and still more preferably 30 to 50 mol.

Structural Unit (3)

It is preferred that the polymer (B) further includes one or more types of structural units having a lactone skeleton or a cyclic carbonate skeleton represented by the following formula (hereinafter, may be also referred to as "structural unit (3)"). When the polymer (B) includes the structural unit (3), adhesiveness and the like of the resultant resist film can be improved.

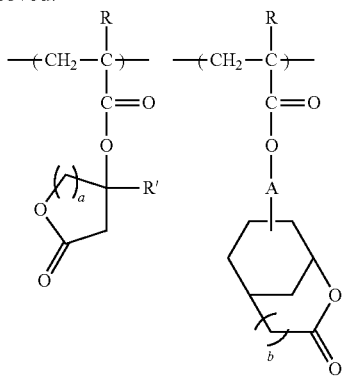

-continued

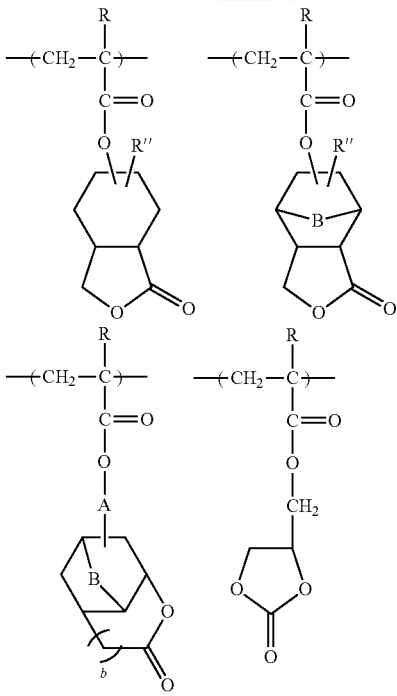

In the above formulae, R and R' each independently represent a hydrogen atom or a methyl group; R" represents a hydrogen atom or a methoxy group; A represents a single bond or a methylene group, B represents a methylene group or an oxygen atom; and a and b are each independently, 0 or 1.

The structural unit (3) is particularly preferably a structural unit represented by any one of the following formulae.

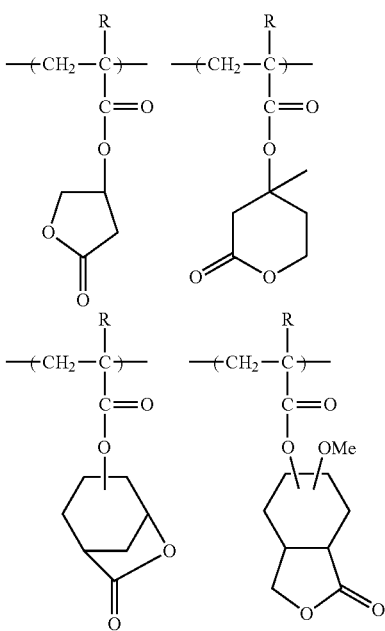

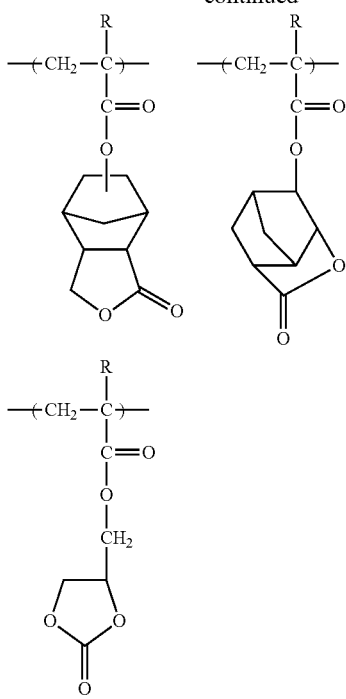

In the above formulae, R represents a hydrogen atom or a methyl group.

The content of the structural unit (3) in the polymer (B) is preferably 30 to 70 mol %, and more preferably 35 to 55 mol.

Structural Unit (4)

In addition, the polymer (B) may include a structural unit (4) having a functional group represented by any one of the following formulae (more preferably, a hydroxyl group).

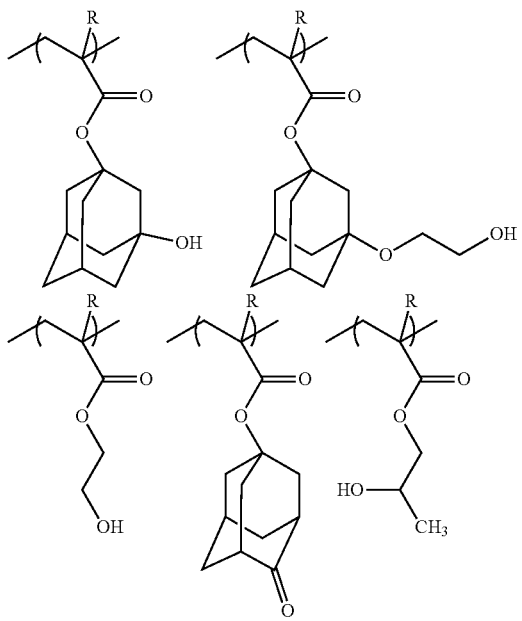

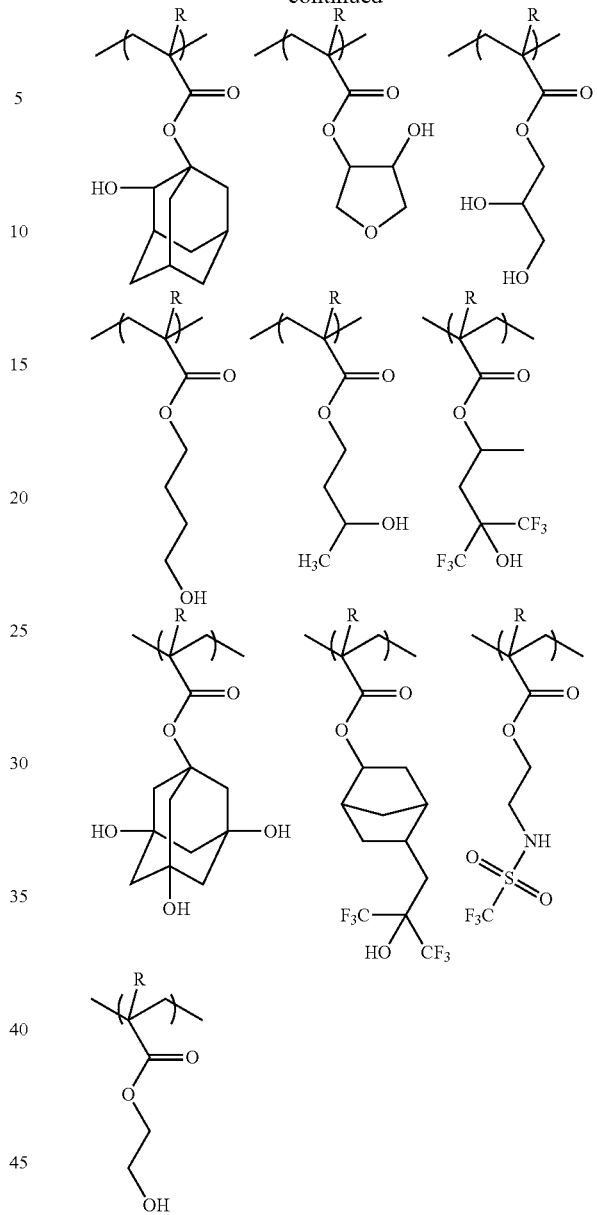

In the above formulae, R represents a hydrogen atom or a methyl group.

The content of the structural unit (4) in the polymer (B) is preferably 3 to 20 mol %, and more preferably 5 to 15 mol %.

Furthermore, the acid-labile group-containing polymer particularly suitably used for the positive radiation-sensitive resin composition for which an F2 excimer laser is employed is exemplified by those described in paragraph [0136] to paragraph [0147] of WO2009/051088.

In a case in which the acid-labile group-containing polymer is produced by polymerization of a polymerizable unsaturated monomer or via such polymerization, a branched structure may be introduced into the polymer by way of a unit derived from a polyfunctional monomer having at least two polymerizable unsaturated bonds, and/or an acetal crosslinking group. By introducing such a branched structure, heat resistance of the acid-labile group-containing polymer can be improved.

In this case, a percentage of introduction of the branched structure into the acid-labile group-containing polymer may be appropriately predetermined according to the type of the branched structure or the polymer to which the structure is introduced, and is preferably no greater than 10 mol % with respect to the entire structural units.

The polymer (B) (acid-labile group-containing polymer) may further have other structural unit. Examples of the other repeating unit include vinyl aromatic compounds such as styrene and α-methylstyrene; structural units derived by cleaving a polymerizable unsaturated bond of (meth)acrylate esters such as butyl (meth)acrylate, adamantyl (meth)acrylate or 2-methyladamantyl(meth)acrylate, and the like.

The molecular weight of the polymer (B) (i.e., acid-labile group-containing polymer) is not particularly limited, and may be appropriately selected. The polystyrene equivalent weight-molecular weight (hereinafter, may be referred to as "Mw") as determined by gel permeation chromatography (GPC) is typically 1,000 to 500,000, preferably 2,000 to 400,000, and more preferably 3,000 to 300,000.

In addition, the Mw of the acid-labile group-containing polymer not having a branched structure is preferably 1,000 to 150,000 and more preferably 3,000 to 100,000, whereas the Mw of the acid-labile group-containing polymer (B1) having a branched structure is preferably 5,000 to 500,000 and more preferably 8,000 to 300,000. By using the acid-labile group-containing polymer having the Mw falling within this range, the resultant resist can be superior in developability with an alkali.

Also, a ratio (Mw/Mn) of the Mw to a polystyrene equivalent number average molecular weight as determined by GPC (hereinafter, may be referred to as "Mn") of the acid-labile group-containing polymer is not particularly limited, and may be appropriately selected. The ratio (Mw/Mn) of the acid-labile group-containing polymer is typically 1 to 10, preferably 1 to 8, and more preferably 1 to 5. When the acid-labile group-containing polymer having the ratio of Mw/Mn falling within this range, the resulting resist can have superior resolving ability. In the positive radiation-sensitive resin composition of the embodiment of the present invention, the acid-labile group-containing polymer may be used either alone, or as a mixture of two or more thereof.

Although the production method of acid-labile group-containing polymer is not particularly limited, the acid-labile group-containing polymer may be produced by, for example, a method in which one or more types of acid-labile groups is/are introduced into an acidic functional group in an alkali-soluble polymer produced beforehand; a method in which one or more types of polymerizable unsaturated monomers having an acid-labile group is/are polymerized occasionally together with one or more other polymerizable unsaturated monomer(s); a method in which one or more types of polycondensible components having an acid-labile group is/are polycondensed occasionally together with other polycondensible component, or the like.

In the polymerization of the polymerizable unsaturated monomer in producing the alkali-soluble polymer, and the polymerization of the polymerizable unsaturated monomer having an acid-labile group, an adequate polymerization system such as block polymerization, solution polymerization, precipitation polymerization, emulsion polymerization, suspension polymerization or block-suspension polymerization may be carried out with a polymerization initiator or polymerization catalyst such as a radical polymerization initiator, an anion polymerization catalyst, a coordinated anion polymerization catalyst or a cation polymerization catalyst appropriately selected in accordance with the polymerizable unsaturated monomer and the type of the reaction medium employed, and the like.

Moreover, polycondensation of the polycondensible component having an acid-labile group may be carried out in a water medium or a mixed medium of water and a hydrophilic solvent in the presence of preferably an acidic catalyst.

The amount of the radiation-sensitive acid generating agent used in the positive radiation-sensitive resin composition may be variously predetermined according to characteristics desired for the resist, and may be preferably 0.001 to 70 parts by mass, more preferably 0.01 to 50 parts by mass, and particularly preferably 0.1 to 20 parts by mass with respect to 100 parts by mass of the acid-labile group-containing polymer. In this instance, when the amount of the radiation-sensitive acid generating agent is no less than 0.001 parts by mass, deterioration of sensitivity and resolution can be inhibited, whereas when the amount is no greater than 70 parts by mass, deterioration of coating properties and pattern configuration of the resist can be inhibited.

(B2) Alkali-Soluble Polymer

Examples of the alkali-soluble polymer include addition polymerization polymers having a structural unit represented by the following formula (17) (hereinafter, may be referred to as "structural unit (17)"), a structural unit represented by the following formula (18) (hereinafter, may be referred to as "structural unit (18)") and a structural unit represented by the following formula (19) (hereinafter, may be referred to as "structural unit (19)") or a combination thereof, and the like.

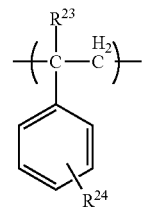

(17)

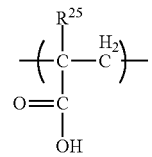

(18)

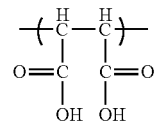

(19)

In the above formulae (17) and (18), $R^{23}$ and $R^{25}$ each independently represent a hydrogen atom or a methyl group; and $R^{24}$ represents a hydroxyl group, a carboxyl group, —$R^{26}$COOH, —O$R^{26}$COOH, —OCO$R^{26}$COOH or COO$R^{26}$COOH (wherein each of $R^{26}$ independently represents —$(CH_2)_e$—, wherein e is an integer of 1 to 4).

The alkali-soluble polymer may be constituted with the structural unit (17), the structural unit (18) or the structural unit (19) alone, but one or more types of other structural units may be further included as long as the polymer produced is soluble in an alkaline developer solution. Examples of the other structural unit include those similar to the other structural units in the acid-labile group-containing polymer described above.

The total content of the structural unit (17), structural unit (18) and structural unit (19) in the alkali-soluble polymer cannot be simply defined depending on the type of the other structural unit which may be included as needed, but is preferably 10 to 100 mol %, and more preferably 20 to 100 mol %.

The alkali-soluble polymer may be used also as a hydrogenated product in the case in which a repeating unit having a carbon-carbon unsaturated bond such as the structural unit (17) is included. The hydrogenation percentage in this case is typically no greater than 70%, preferably no greater than 50%, and more preferably no greater than 40% with respect to the carbon-carbon unsaturated bonds included in corresponding structural units. In this instance, when the hydrogenation percentage exceeds 70%, developability with an alkali of the alkali-soluble polymer may be deteriorated.

The alkali-soluble polymer is particularly preferably a polymer that includes poly(4-hydroxystyrene), a 4-hydroxystyrene/4-hydroxy-α-methylstyrene copolymer, a 4-hydroxystyrene/styrene copolymer or the like as a principal component.

The Mw of the alkali-soluble polymer radiation-sensitive resin composition may vary depending on desired characteristics, and is typically 1,000 to 150,000, and preferably 3,000 to 100,000.

In the radiation-sensitive resin composition of the embodiment of the present invention, the alkali-soluble polymer may be used either alone or as a mixture of two or more thereof.

Crosslinking Agent

In the negative radiation-sensitive polymer composition, a compound that enables the alkali-soluble polymer to be crosslinked in the presence of an acid (hereinafter, may be referred to as "crosslinking agent") may be blended. The crosslinking agent is exemplified by compounds having one or more functional groups having crosslinking reactivity with the alkali-soluble polymer(hereinafter, may be referred to as "crosslinkable functional group").

Examples of the crosslinkable functional group include a glycidyl ether group, a glycidyl ester group, a glycidylamino group, a methoxymethyl group, an ethoxymethyl group, a benzyloxymethyl group, an acetoxymethyl group, a benzoyloxymethyl group, a formyl group, an acetyl group, a vinyl group, an isopropenyl group, a (dimethylamino)methyl group, a (diethylamino)methyl group, a (dimethylolamino)methyl group, a (diethylolamino)methyl group, a morpholinomethyl group, and the like.

Examples of the crosslinking agent include bisphenol A type epoxy compounds, bisphenol F type epoxy compounds, bisphenol S type epoxy compounds, novolak polymer type epoxy compounds, resol polymer type epoxy compounds, poly(hydroxystyrene) type epoxy compounds, methylol group-containing melamine compounds, methylol group-containing benzoguanamine compounds, methylol group-containing urea compounds, methylol group-containing phenol compounds, alkoxyalkyl group-containing melamine compounds, alkoxyalkyl group-containing benzoguanamine compounds, alkoxyalkyl group-containing urea compounds, alkoxyalkyl group-containing phenol compounds, carboxymethyl group-containing melamine polymers, carboxymethyl group-containing benzoguanamine polymers, carboxymethyl group-containing urea polymers, carboxymethyl group-containing phenol polymers, carboxymethyl group-containing melamine compounds, carboxymethyl group-containing benzoguanamine compounds, carboxymethyl group-containing urea compounds, carboxymethyl group-containing phenol compounds, and the like.

Among these crosslinking agents, methylol group-containing phenol compounds, methoxymethyl group-containing melamine compounds, methoxymethyl group-containing phenol compounds, methoxymethyl group-containing glycoluril compounds, methoxymethyl group-containing urea compounds and acetoxymethyl group-containing phenol compounds are preferred, and further preferably methoxymethyl group-containing melamine compounds (for example, hexamethoxymethylmelamine, etc.), methoxymethyl group-containing glycoluril compounds, methoxymethyl group-containing urea compounds, and the like. The methoxymethyl group-containing melamine compound is commercially available under the trade names of CYMEL 300, CYMEL 301, CYMEL 303 and CYMEL 305 (all manufactured by Mitsui-Cyanamid, Ltd.) and the like; the methoxymethyl group-containing glycoluril compound is commercially available under the trade name of CYMEL 1174 (manufactured by Mitsui-Cyanamid, Ltd.) and the like; and the methoxymethyl group-containing urea compound is commercially available under the trade name of MX290 (manufactured by SANWA Chemical Co., Ltd) and the like, respectively.

In addition, as the crosslinking agent, a polymer produced by substituting for the crosslinkable functional group, hydrogen atoms of the oxygen-containing functional group in the alkali-soluble polymer to impart a property as a crosslinking agent may be also suitably used. It is impossible to categorically define the percentage introduction of the crosslinkable functional group in this case depending on the type of the crosslinkable functional group and the alkali-soluble polymer into which the group is introduced, but the percentage introduction is typically 5 to 60 mol %, preferably 10 to 50 mol %, and more preferably 15 to 40 mol % with respect to all the oxygen-containing functional groups in the alkali-soluble polymer. In this instance, the percentage introduction of the crosslinkable functional group being less than 5 mol % is likely to result in a decrease in the percentage of residual film, meandering and swelling of the pattern, and the like. To the contrary, when the percentage introduction is beyond 60 mol %, the alkali developability tends to be deteriorated.

The crosslinking agent is particularly preferably a methoxymethyl group-containing compound, and more specifically, dimethoxymethylurea, tetramethoxymethyl glycoluril and the like are preferred. In the negative radiation-sensitive resin composition of the embodiment of the present invention, the crosslinking agent may be used either alone, or as a mixture of two or more types thereof.

The amount of the radiation-sensitive acid generating agent in the negative radiation-sensitive resin composition is preferably 0.01 to 70 parts by mass, more preferably 0.1 to 50 parts by mass, and particularly preferably 0.5 to 20 parts by mass with respect to 100 parts by mass of the alkali-soluble polymer. In this case, when the amount of the radiation-sensitive acid generating agent is less than 0.01 parts by mass, sensitivity and/or resolution tend to be deteriorated. Whereas the amount of the radiation-sensitive acid generating agent exceeding 70 parts by mass is likely to result in deterioration of coating properties and/or pattern configuration of the resist.

The amount of the crosslinking agent used is preferably 5 to 95 parts by mass, more preferably 15 to 85 parts by mass, and particularly preferably 20 to 75 parts by mass with respect to 100 parts by mass of the alkali-soluble polymer. In this instance, when the amount of the crosslinking agent used is less than 5 parts by mass, a decrease in the percentage of residual film, meandering and swelling of the pattern, and the like are likely to be caused, whereas, when the amount is beyond 95 parts by mass, the alkali developability tends to be deteriorated.

(C) Polymer

The radiation-sensitive resin composition of the embodiment of the present invention may also contain (C) a polymer that includes a fluorine atom. When a resist film is formed using the composition containing the polymer (B) and the polymer (C), the distribution of the polymer (C) is likely to increase on the surface of the resist film resulting from the oil repellency of the polymer (C). In other words, the polymer (C) is unevenly distributed in the surface layer of the resist film. Therefore, when the polymer (C) is used, it is not necessary to separately form an upper layer film for the purpose of blocking the resist film from the medium for liquid immersion, and thus the radiation-sensitive resin composition can be suitably used in a liquid immersion lithography process.

Structural Unit (C1)

The polymer (C) is not particularly limited as long as it includes a fluorine atom in the molecule, and preferably has a structural unit that includes a fluorine atom (hereinafter, may be referred to as "structural unit (C1)"). Specific examples of the structural unit (C1) include structural units represented by the following formulae (a1-1) to (a1-3) (hereinafter, may be merely referred to as "structural units (a1-1) to (a1-3)").

When the polymer (C) has any of the structural units (a1-1) to (a1-3), elution of an acid generating agent, an acid diffusion control agent, etc. in the resist coating film into a liquid for liquid immersion lithography is suppressed, and water droplet originated from a liquid for liquid immersion lithography is less likely to remain on the resist coating film due to improvement of a receding contact angle between the resist coating film and the liquid for liquid immersion lithography, whereby generation of defects resulting from a liquid for liquid immersion lithography can be inhibited.

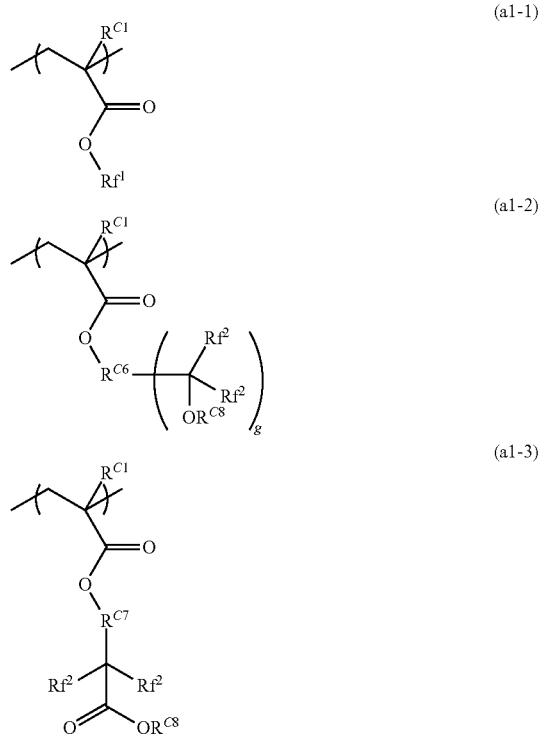

In the formulae (a1-1) to (a1-3), $R^{C1}$s each independently represent a hydrogen atom, a methyl group or a trifluoromethyl group. In the formula (a1-1), $Rf^1$ represents a fluorinated alkyl group having 1 to 30 carbon atoms. In the formula (a1-2), $R^{C6}$ represents a linking group having a valency of (g+1); and g is an integer of 1 to 3. In the formula (a1-3), $R^{C7}$ represents a divalent linking group. In the formulae (a1-2) and (a2-3), $R^{C8}$ represents a hydrogen atom or a monovalent organic group; and $Rf^2$s each independently represent a hydrogen atom, a fluorine atom or a fluorinated alkyl group having 1 to 30 carbon atoms, but any case where all $Rf^2$s represent a hydrogen atom is excluded.

Structural Unit (a 1-1)

$Rf^1$ in the above formula (a1-1) is exemplified by a linear or branched alkyl group having 1 to 6 carbon atoms substituted with at least one or more fluorine atoms, a monovalent alicyclic hydrocarbon group having 4 to 20 carbon atoms substituted with at least one or more fluorine atoms, or a group derived therefrom.

The linear or branched alkyl group having 1 to 6 carbon atoms substituted with at least one or more fluorine atoms, the monovalent alicyclic hydrocarbon group having 4 to 20 carbon atoms substituted with at least one or more fluorine atoms or the group derived therefrom is as exemplified above in connection with Rf above.

Examples of preferred monomers which give the above repeating unit (a1-1) include (meth)acrylic acid trifluoromethyl ester, (meth)acrylic acid 2,2,2-trifluoroethyl ester, (meth)acrylic acid perfluoroethyl ester, (meth)acrylic acid perfluoro-n-propyl ester, (meth)acrylic acid perfluoro-i-propyl ester, (meth)acrylic acid perfluoro-n-butyl ester, (meth)acrylic acid perfluoro-I-butyl ester, (meth)acrylic acid perfluoro-t-butyl ester, (meth)acrylic acid 2-(1,1,1,3,3,3-hexafluoropropyl)ester, (meth)acrylic acid 1-(2,2,3,3,4,4,5,5-octafluoropentyl)ester, (meth)acrylic acid perfluorocyclohexylmethyl ester, (meth)acrylic acid 1-(2,2,3,3,3-pentafluoropropyl)ester, (meth)acrylic acid 1-(3,3,4,4,5,5,6,6,7,7,8,8,9,9,10,10,10-heptadecafluorodecyl)ester, (meth)acrylic acid 1-(5-trifluoromethyl-3,3,4,4,5,6,6,6-octafluorohexyl)ester, and the like.

Structural Units (a1-2) and (a1-3)

The polymer (C) may include a structural unit (a1-2) and/or a structural unit (a1-3) as the structural unit that includes a fluorine atom.

In the above formula (a1-2) or (a1-3), $R^{C8}$ represents a hydrogen atom or a monovalent organic group. Examples of the monovalent organic group include monovalent hydrocarbon groups having 1 to 30 carbon atoms, acid-labile groups, and alkali-labile groups.

The monovalent hydrocarbon group having 1 to 30 carbon atoms is exemplified by linear or branched monovalent hydrocarbon groups having 1 to 10 carbon atoms, and monovalent cyclic hydrocarbon groups having 3 to 30 carbon atoms. With respect to these hydrocarbon groups, the definition of the hydrocarbon group in connection with $R^1$ above may be directly applied, but those involved in acid-labile groups and alkali-labile groups described later are excluded.

Moreover, the hydrocarbon group may have a substituent. With respect to the substituent, the definition of the substituent which may be included in $R^1$ described above may be directly applied.

The "acid-labile group" as herein referred to means a group that substituted for a hydrogen atom in a polar functional group of, for example, a hydroxyl group, a carboxyl group or the like, and that is dissociated in the presence of an acid.

Specific examples of the acid-labile group include a t-butoxycarbonyl group, a tetrahydropyranyl group, a tetrahydrofuranyl group, a (thiotetrahydropyranylsulfanyl)methyl group, a (thiotetrahydrofuranylsulfanyl)methyl group, as well as an alkoxy-substituted methyl group, an alkylsulfanyl-substituted methyl group, and the like. It is to be noted that the alkoxyl group (substituent) in the alkoxy-substituted methyl group is exemplified by an alkoxyl group having 1 to 4 carbon atoms. In addition, the alkyl group (substituent) in the alkylsulfanyl-substituted methyl group is exemplified by an alkyl group having 1 to 4 carbon atoms.

Furthermore, the acid-labile group is exemplified by a group represented by a general formula of: [—C(R)$_3$]. Wherein, in the formula, three Rs may be similarly defined to R$^{11}$ in the above formula (2).

In addition, among these acid-labile groups, the group represented by the formula of: [—C(R)$_3$], a t-butoxycarbonyl group, an alkoxy-substituted methyl group and the like are preferred. In particular, in the structural unit (a1-2), a t-butoxycarbonyl group and an alkoxy-substituted methyl group are preferred. In the structural unit (a1-3), an alkoxy-substituted methyl group and the group represented by the formula of: [—C(R)$_3$] are preferred.

When the structural unit (a1-2) or structural unit (a1-3) having an acid-labile group is used, use in combination with the polymer (B 1) described above provides a preferable positive radiation-sensitive resin composition since the improvement of the solubility of the polymer (C) at the site exposed with a radioactive ray is enabled. This benefit is believed to result from generation of a polar group through a reaction with an acid generated at a light-exposed site of the resist coating film in the exposure step of a method for forming a resist pattern described later.

The "alkali-labile group" as referred to means a group that substitutes for a hydrogen atom in a polar functional group such as for example, a hydroxyl group or a carboxyl group and is dissociated in the presence of an alkali.

Such an alkali-labile group is not particularly limited as long as the aforementioned properties are exhibited, and the alkali-labile group in the above formula (a1-2) is exemplified by groups represented by the following formula (R1-1).

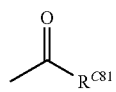

(R1-1)

In the above formula (R1-1), R$^{C81}$ represents a hydrocarbon group having 1 to 10 carbon atoms in which at least one hydrogen atom(s) is/are substituted by a fluorine atom. With respect to R$^{C81}$, the definition of Rf$^1$ described above may be applied.

R$^{C81}$ is more preferably a linear or branched perfluoroalkyl group having 1 to 10 carbon atoms in which all hydrogen atoms in the hydrocarbon group are substituted by a fluorine atom, and particularly preferably a trifluoromethyl group.

Furthermore, alkali-labile group in the above formula (a1-3) is exemplified by groups represented the following formulae (R1-2) to (R1-4).

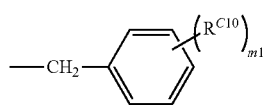

(R1-2)

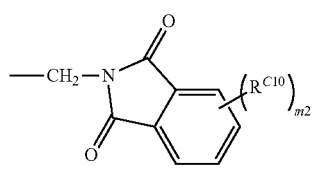

(R1-3)

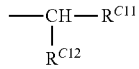

(R1-4)

In the above formulae (R1-2) and (R1-3), R$^{C10}$ represents a halogen atom, or an alkyl group, alkoxyl group, acyl group, or acyloxy group having 1 to 10 carbon atoms, and may be identical or different in a case where R$^{C10}$ is present in a plurality of number; m$_1$ is an integer of 0 to 5; and m$_2$ is an integer of 0 to 4.

In the above formula (R1-4), R$^{C11}$ and R$^{C12}$ each independently represent a hydrogen atom or an alkyl group having 1 to 10 carbon atoms, and optionally R$^{C11}$ and R$^{C12}$ bond to one another to taken together represent an alicyclic structure having 4 to 20 carbon atoms.

In the above formulae (R1-2) and (R1-3), examples of the halogen atom represented by R$^{C10}$ include a fluorine atom, a chlorine atom, a bromine atom, an iodine atom, and the like. Of these, a fluorine atom is preferred.

In the above formulae (R1-2) and (R1-3), with respect to the alkyl group having 1 to 10 carbon atoms represented by R$^{C10}$, the definition of R$^1$ described above may be applied.

In the above formula (R1-4), the alkyl group having 1 to 10 carbon atoms represented by R$^{C11}$ or R$^{C12}$ include groups exemplified in connection with R$^{C10}$ above.

In addition, examples of the alicyclic structure taken together represented by R$^{C11}$ and R$^{C12}$ bonded to one another together with the carbon atom to which R$^{C11}$ and R$^{C12}$ each bond include a cyclopentyl group, a cyclopentylmethyl group, a 1-(1-cyclopentylethyl) group, a 1-(2-cyclopentylethyl) group, a cyclohexyl group, a cyclohexylmethyl group, a 1-(1-cyclohexylethyl) group, a 1-(2-cyclohexylethyl) group, a cycloheptyl group, a cycloheptylmethyl group, a 1-(1-cycloheptylethyl) group, a 1-(2-cycloheptylethyl) group, a 2-norbornyl group, and the like.

Specific examples of the group represented by the above formula (R1-4) include a methyl group, an ethyl group, a 1-propyl group, a 2-propyl group, a 1-butyl group, a 2-butyl group, a 1-pentyl group, a 2-pentyl group, a 3-pentyl group, a 1-(2-methylbutyl) group, a 1-(3-methylbutyl) group, a 2-(3-methylbutyl) group, a neopentyl group, a 1-hexyl group, a 2-hexyl group, a 3-hexyl group, a 1-(2-methylpentyl) group, a 1-(3-methylpentyl) group, a 1-(4-methylpentyl) group, a 2-(3-methylpentyl) group, a 2-(4-methylpentyl) group, a 3-(2-methylpentyl) group, and the like. Of these, a methyl group, an ethyl group, a 1-propyl group, a 2-propyl group, a 1-butyl group and a 2-butyl group are preferred.

Including one having the alkali-labile group in the structural unit (a1-2) or the structural unit (a1-3) in the polymer (C) is preferred since an affinity of the polymer (C) to a developer solution can be improved. This benefit is believed to result from generation of a polar group through a reaction of the polymer (C) with a developer solution in the development step of a method for forming a pattern described later.

In the above formulae (a1-2) and (a1-3), in the case in which R$^{C8}$ represents a hydrogen atom, the structural units (a1-2) and (a1-3) will have a hydroxyl group and a carboxy group which are each a polar group. When the polymer (C) has such a structural unit, an affinity of the polymer (C) to the developer solution can be improved in the development step of a method for forming a pattern described later.

In the above formula (a1-2), R$^{C6}$ represents a linking group having a valency of (g+1). Such a group is exemplified by a single bond, or a hydrocarbon group having 1 to 30 carbon atoms and having a valency of (g+1). Alternatively, combinations of any of these hydrocarbon groups with a sulfur atom, an imino group, a carbonyl group, —CO—O— or —CO—NH— may be exemplified. "g" is an integer of 1 to 3. When g is 2 or 3, structures represented by:

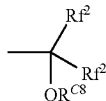

in the formula (a1-2) are each independent.

Examples of $R^{C6}$ having a chain structure include hydrocarbon groups having a valency of (g+1) and having a structure obtained by removing (g+1) hydrogen atoms from a chain hydrocarbon having 1 to 10 carbon atoms such as methane, ethane, propane, butane, 2-methylpropane, pentane, 2-methylbutane, 2,2-dimethylpropane, hexane, heptane, octane, nonane or decane, and the like.

Moreover, examples of $R^{C6}$ having a cyclic structure include hydrocarbon groups having a valency of (g+1) and having a structure obtained by removing (g+1) hydrogen atoms from an alicyclic hydrocarbon having 4 to 20 carbon atoms such as cyclobutane, cyclopentane, cyclohexane, bicyclo[2.2.1]heptane, bicyclo[2.2.2]octane, tricyclo[5.2.1.02,6]decane or tricyclo[3.3.1.13,7]decane; and hydrocarbon groups having a valency of (g+1) and having a structure obtained by removing (g+1) hydrogen atoms from an aromatic hydrocarbon having 6 to 30 carbon atoms such as benzene or naphthalene; and the like.

In addition, among $R^{C6}$s, those having a structure that includes an oxygen atom, a sulfur atom, an imino group, a carbonyl group, —CO—O— or —CO—NH— are exemplified by groups represented by the following general formulae.

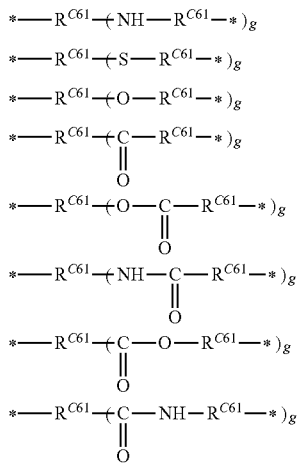

In the above formulae, $R^{C61}$ each independently represent a single bond, a divalent chain hydrocarbon group having 1 to 10 carbon atoms, a divalent cyclic hydrocarbon group having 4 to 20 carbon atoms or a divalent aromatic hydrocarbon group having 6 to 30 carbon atoms. Among those represented by $R^{C61}$, with respect to the divalent chain hydrocarbon group having 1 to 10 carbon atoms, the divalent cyclic hydrocarbon group having 4 to 20 carbon atoms and the divalent aromatic hydrocarbon group having 6 to 30 carbon atoms, the definition in connection with $R^{C6}$ may be directly applied.

In addition, $R^{C6}$ may have a substituent. As such a substituent, the definition of the substituent which may be included in $R^1$ may be applied.

The linking group represented by $R^{C7}$ in the above general formula (a1-3) may be similarly defined to $R^{C6}$ described above wherein g is 1.

In the above formula (a1-2) or (a1-3), $Rf^2$ represents a hydrogen atom, a fluorine atom or a fluorinated hydrocarbon group having 1 to 30 carbon atoms, wherein, any case where all $Rf^2$s represent a hydrogen atom is excluded. With respect to the fluorinated hydrocarbon group having 1 to 30 carbon atoms represented by $Rf^2$, the definition in connection with $Rf^1$ may be directly applied.

In the above formulae (a1-2) and (a1-3), a partial structure represented by:

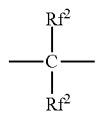

is exemplified by those represented by the following formulae (1) to (5). Of these, in the above formula (a1-2), a structure represented by the following formula (5) is preferred, whereas in the above formula (a1-3), a structure represented by the following formula (3) is preferred.

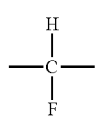 (1)

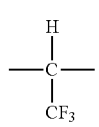 (2)

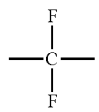 (3)

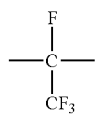 (4)

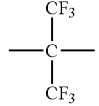 (5)

Specific examples of the structural unit (a1-2) include those represented by the following formulae (a1-2-1) and (a1-2-2).

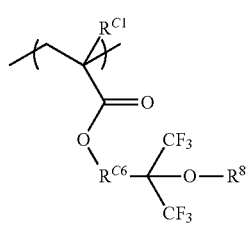 (a1-2-1)

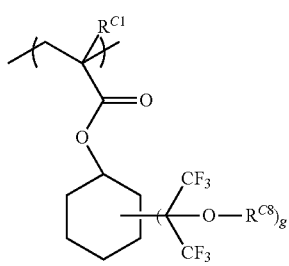
(a1-2-2)

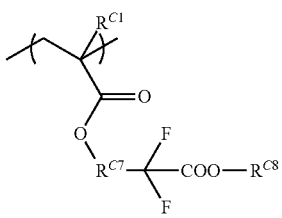
(a1-3-1)

In the above formulae (a1-2-1) and (a1-2-2), $R^{C1}$, $R^{C6}$, $R^{C8}$ and g are as defined in connection with the above general formula (a2-1).

Examples of compounds that give such a structural unit include those represented by the following formulae.

In the above formula (a1-3-1), $R^{C1}$, $R^{C7}$ and $R^{C8}$ are as defined in the above general formula (a1-3). Examples of compounds that give such a structural unit include those represented by the following formulae.

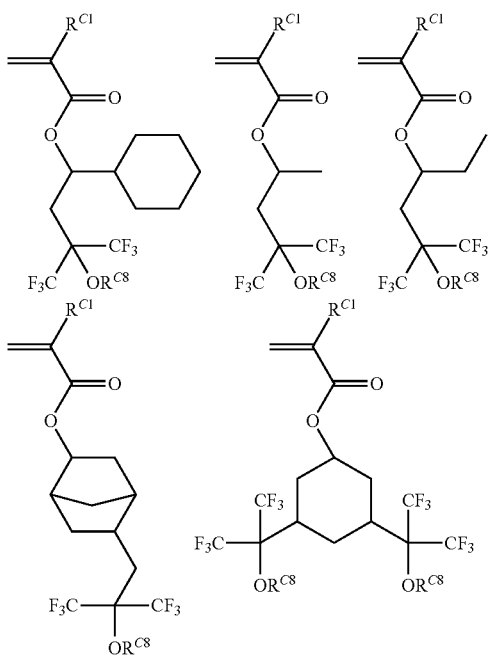

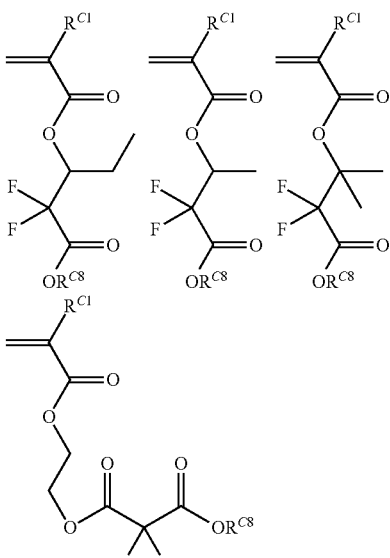

In the above formulae, $R^{C1}$, and $R^{C8}$ are similarly defined to those in the above general formula (a1-2).

The compound represented by the above formula, in which $R^{C8}$ represents an acid-labile group and/or an alkali-labile group can be synthesized using as a raw material, for example, a compound represented by each formula in which $R^{C8}$ represents a hydrogen atom. Referring to an exemplary compound in which $R^{C8}$ is represented by the above formula (R1-1), the intended compound represented by the above formula can be formed by fluoroacylating a compound represented by each formula in which $R^{C8}$ represents a hydrogen atom according to a conventionally well-known method. For example, 1) a method including allowing an alcohol and a fluorocarboxylic acid to be condensed in the presence of an acid, thereby permitting esterification, 2) a method including allowing an alcohol and a fluorocarboxylic acid halide to be condensed in the presence of a base, thereby permitting esterification, and the like may be exemplified.

Specific examples of the structural unit (a1-3) include those represented by the following formula.

In the above formula (a1-3-1), $R^{C1}$ and $R^{C8}$ are as defined in the above general formula (a1-3).

The compound represented by the above formula, in which $R^{C8}$ represents an acid-labile group or an alkali-labile group can be synthesized using as a raw material, for example, a compound represented by each formula in which $R^{C8}$ represents a hydrogen atom, or a derivative thereof. Referring to an exemplary compound in which $R^{C8}$ is represented by the above formula (R1-4), this compound can be obtained by allowing, for example, a compound represented by the following general formula (m-2-3) to react with a compound represented by the following formula (m-2-4-3).

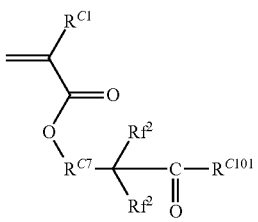
(m-2-3)

In the general formula (m-2-3), $R^{C1}$, $R^{C7}$ and $Rf^2$ are as defined in connection with the general formula (a1-3); and $R^{C101}$ represents a hydroxyl group or a halogen atom.

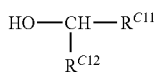
(m-2-4-3)

In the general formula (m-2-4-3), $R^{C11}$ and $R^{C12}$ are as defined in connection with the general formula (R1-4).

The polymer (C) may include only one type of the above structural units (a1-1) to (a1-3), or two or more thereof, and preferably has at least two types of the structural units (a1-1) to (a1-3). Any combination of the structural unit (a1-2) and the structural unit (a1-3) is particularly preferred. In addition, among the structural units (a1-1) to (a1-3), it is preferred to include the structural unit (a1-3).

The polymer (C) may further include in addition to the above structural unit (C1): a structural unit that has an acid-labile group other than the structural unit (C1) (hereinafter, may be referred to as "structural unit (C2)"); a structural unit (C3) that has an alkali-soluble group excluding those corresponding to the above structural unit (C1) (hereinafter, may be merely referred to as "structural unit (C3)"); or a structural unit (C4) that has a lactone skeleton (hereinafter, may be merely referred to as "structural unit (C4)").

Structural Unit (C2)

When a polymer including the structural unit (C2) is used as the polymer (C), use in combination with the polymer (B) is particularly preferred for a positive radiation-sensitive resin composition. In this case, the difference between an advancing contact angle and a receding contact angle of the photoresist film can be decreased, thereby allowing for attaining acceleration of a scanning speed in an exposure. The structural unit (C2) is preferably, for example, a structural unit represented by the above formula (2).

In addition, the structural unit (C2) is particularly preferably a structural unit represented by the following formula (C2-1-1) among the structural units represented by the above formula (2).

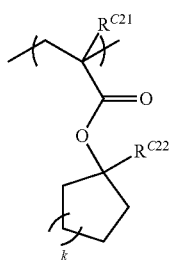
(C2-1-1)

In the above formula (C2-1-1), $R^{C21}$ represents a hydrogen atom, a methyl group, a trifluoromethyl group or a hydroxymethyl group; $R^{C22}$ represents a linear or branched alkyl group having 1 to 4 carbon atoms; and k is an integer of 1 to 4.

In the above formula (C2-1-1), examples of the linear or branched alkyl group having 1 to 4 carbon atoms represented by $R^{C22}$ include a methyl group, an ethyl group, a n-propyl group, an i-propyl group, a n-butyl group, a 2-methylpropyl group, a 1-methylpropyl group, a t-butyl group, and the like.

The polymer (C) may include the structural unit (C2) either one type alone or in combination of two or more types thereof. The polymer (C) which may be used further include the structural unit (C3) or the structural unit (C4) in addition to the structural units (C1) and (C2). In this case, solubility in a developer solution can be improved.

Structural Unit (C3)

The alkali-soluble group in the structural unit (C3) is preferably a functional group having a hydrogen atom and having a pKa of 4 to 11, because the improvement of the solubility in a developer solution may be expected. Specific examples of such a functional group include functional groups represented by the following formula (C3a) and formula (C3b), and the like.

In the above formula (C3a), $R^{C23}$ represents a hydrocarbon group having 1 to 10 carbon atoms substituted with a fluorine atom.

In the above formula (C3a), the hydrocarbon group having 1 to 10 carbon atoms substituted with a fluorine atom represented by $R^{C23}$ is not particularly limited as long as one, or two or more hydrogen atoms in the hydrocarbon group having 1 to 10 carbon atoms is/are substituted by a fluorine atom, and for example, a trifluoromethyl group and the like are preferred.

It is to be noted that the main chain skeleton of the structural unit (C3) is not particularly limited, and is preferably a skeleton of a methacrylic acid ester, an acrylic acid ester, or an α-trifluoro acrylic acid ester.

Examples of the structural unit (C3) include structural units derived from compounds represented by the general formulae (C3a-1) and (C3b-1).

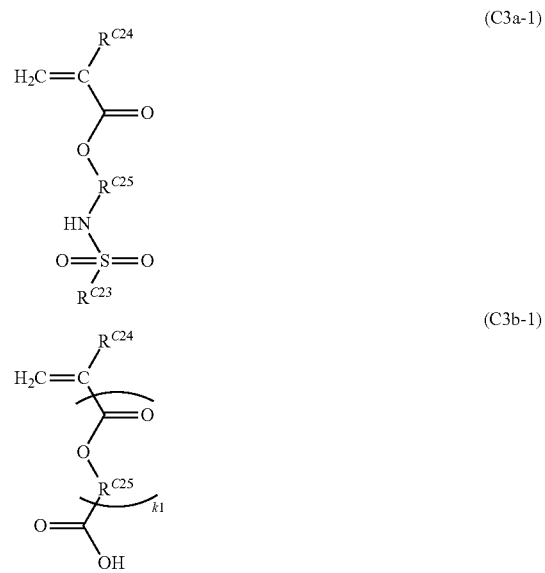

In the general formulae (C3a-1) and (C3b-1), $R^{C24}$ represents a hydrogen atom, a methyl group, or a trifluoromethyl group; $R^{C25}$ represents a divalent linking group; $R^{C23}$ represents a hydrocarbon group having 1 to 10 carbon atoms substituted with a fluorine atom; and k1 is 0 or 1.

In the above formula (C3a-1) and (C3b-1), with respect to the group represented by $R^{C25}$, a similar definition of $R^{C7}$ in the above formula (a1-3) may be applied. Furthermore, in the above formula (C3a-1), with respect to the group represented by $R^{C23}$, a similar definition of $R^{C23}$ in the above formula (C3a) may be applied.

The (C) polymer may include the structural unit (C3) either alone or in combination of two or more types thereof.

Structural Unit (C4)

Specifically, the structural unit (C4) is exemplified by a structural unit having a lactone skeleton (hereinafter, may be referred to as "structural unit (C4-1)"). With respect to examples of the structural unit (C4-1), those of the structural unit (3) which may be included in the polymer (B) may be included.

Proportion of Each Structural Unit Included

The proportion of each structural unit included with respect to 100 mol % in total of the entire structural units in the polymer (C) is shown below. The proportion of the structural unit (C1) included is preferably 20 to 90 mol %, and particularly preferably 20 to 80 mol %. In addition, the proportion of the structural unit (C2) included is typically no greater than 80 mol %, preferably 20 to 80 mol %, and more preferably 30 to 70 mol %. The proportion of the structural unit (C2) included falling within this range is particularly preferred in light of a decrease in the difference between the advancing contact angle and the receding contact angle. The proportion of the structural unit (C3) included is typically no greater than 50 mol %, preferably 5 to 30 mol %, and more preferably 5 to 20 mol %. The proportion of the structural unit (C4) included is typically no greater than 50 mol %, preferably 5 to 30 mol %, and more preferably 5 to 20 mol %.

The weight average molecular weight of the polymer (C) in terms of a polystyrene equivalent as determined by a gel permeation chromatography (GPC) method (hereinafter, may be referred to as "Mw") is preferably 1,000 to 50,000, more preferably 1,000 to 40,000, and still more preferably 1,000 to 30,000. When the Mw is less than 1,000, obtaining a photoresist film having a sufficient receding contact angle may fail. On the other hand, when the Mw exceeds 50,000, the developability of the photoresist film may be deteriorated. In addition, a ratio (Mw/Mn) of the Mw to the number average molecular weight in terms of a polystyrene equivalent as determined by a GPC method (hereinafter, may be referred to as "Mn") of the polymer (C) is preferably 1 to 5, and more preferably 1 to 4.

The content of the polymer (C) is preferably 0.1 to 20 parts by mass, more preferably 1 to 10 parts by mass, and particularly preferably 1 to 7.5 parts by mass with respect to 100 parts by mass of the base polymer (B). When the content of the polymer (C) is less than 0.1 parts by mass, the effects achieved by including the polymer (C) may not be sufficiently achieved. On the other hand, when the content is greater than 20 parts by mass, water repellency of the surface of the resist film may be so great that development defects may occur.

The proportion of fluorine atoms incorporated in the polymer (C) is typically no less than 5% by mass, preferably 5 to 50% by mass, and still more preferably 5 to 40% by mass. It is to be noted that the proportion of fluorine atoms incorporated may be determined by $^{13}$C-NMR. When the proportion of fluorine atoms incorporated in the polymer (C) falls within the above range, water repellency of the surface of the photoresist film formed from the photoresist composition containing the polymer (C) and the polymer (B) described above can be improved, and thus it is not necessary to separately form an upper layer film in liquid immersion lithography.

Production Method of Polymer (C)

The polymer (C) may be prepared, for example, by polymerizing a polymerizable unsaturated monomer corresponding to each predetermined structural unit in an appropriate solvent using a radical polymerization initiator such as a hydroperoxide, dialkylperoxide, diacylperoxide, azo compound or the like, in the presence of a chain transfer agent if necessary.

Examples of the solvent used in the polymerization include: alkanes such as n-pentane, n-hexane, n-heptane, n-octane, n-nonane and n-decane; cycloalkanes such as cyclohexane, cycloheptane, cyclooctane, decalin and norbornane; aromatic hydrocarbons such as benzene, toluene, xylene, ethylbenzene and cumene; halogenated hydrocarbons such as chlorobutanes, bromohexanes, dichloroethanes, hexamethylenedibromide and chlorobenzene; saturated carboxylate esters such as ethyl acetate, n-butyl acetate, i-butyl acetate and methyl propionate; ketones such as acetone, 2-butanone, 4-methyl-2-pentanone and 2-heptanone; ethers such as tetrahydrofuran, dimethoxyethanes and diethoxyethanes; alcohols such as methanol, ethanol, 1-propanol, 2-propanol and 4-methyl-2-pentanol, and the like. These solvents may be used either alone, or as a mixture of two or more thereof.

The reaction temperature in the polymerization is typically 40 to 150° C., and preferably 50 to 120° C. The reaction time in the polymerization is typically 1 to 48 hrs, and preferably 1 to 24 hrs.

(D) Acid Diffusion Control Agent

Into the radiation-sensitive resin composition of the embodiment of the present invention is preferably blended an acid diffusion control agent that controls a phenomenon of diffusion in the resist coating film of an acid generated from the radiation-sensitive acid generating agent by exposure, thereby inhibiting an undesired chemical reaction in an unexposed area. By blending such an acid diffusion control agent, storage stability of the radiation-sensitive resin composition can have improved. In addition, the resolution is further improved, and an alteration of a line width of the resist pattern due to varying post-exposure delay (PED) from the exposure to the development process to be prevented. As a result, a radiation-sensitive resin composition that is extremely superior in process stability can be obtained.

Such an acid diffusion control agent is exemplified by those disclosed in WO 2009/051088, in paragraphs [0176] to [0187], and the like.

Examples of the nitrogen-containing compound (α) include: monoalkylamines such as n-hexylamine, n-heptylamine, n-octylamine, n-nonylamine and n-decylamine; dialkylamines such as di-n-butylamine, di-n-pentylamine, di-n-hexylamine, di-n-heptylamine, di-n-octylamine, di-n-nonylamine and di-n-decylamine; trialkylamines such as tri-ethylamine, tri-n-propylamine, tri-n-butylamine, tri-n-pentylamine, tri-n-hexylamine, tri-n-heptylamine, tri-n-octylamine, tri-n-nonylamine and tri-n-decylamine; alkanolamines such as ethanolamine, diethanolamine and tri-ethanolamine; aromatic amines such as aniline, N-methylaniline, N,N-dimethyl aniline, 2-methylaniline, 3-methylaniline, 4-methylaniline, 4-nitroaniline, diphenylamine, triphenylamine and 1-naphthylamine, and the like.

Examples of the nitrogen-containing compound (β) include ethylenediamine, N,N,N',N'-tetramethylethylenediamine, tetramethylenediamine, hexamethylenediamine, N,N,N',N'-tetrakis(2-hydroxyethyl)ethylenediamine, N,N,N',N'-tetrakis(2-hydroxypropyl)ethylenediamine, 4,4'-diaminodiphenylmethane, 4,4'-diaminodiphenyl ether, 4,4'-diaminobenzophenone, 4,4'-diaminodiphenylamine, 2,2'-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, 1,3-bis[1-(4-aminophenyl)-1-methylethyl]benzene, and the like. Examples of the nitrogen-containing compound (γ) include polyethyleneimine, polyallylamine, polymers of N-(2-dimethylaminoethyl)acrylamide, and the like.

Examples of the amide group-containing compound include formamide, N-methylformamide, N,N-dimethylformamide, acetamide, N-methylacetamide, N,N-dimethylacetamide, propionamide, benzamide, pyrrolidone, N-methylpyrrolidone, and the like.

Examples of the urea compound include urea, methylurea, 1,1-dimethylurea, 1,3-dimethylurea, 1,1,3,3-tetramethylurea, 1,3-diphenylurea, tri-n-butylthiourea, and the like.

Examples of the nitrogen-containing heterocyclic compound include: imidazoles such as imidazole, benzimidazole, 2-methylimidazole, 4-methylimidazole, 1,2-dimethyl imidazole, 2-phenylimidazole, 4-phenylimidazole, 4-methyl-2-phenylimidazole and 2-phenylbenzimidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, nicotinic amide, quinoline, 8-oxyquinoline and acridine, as well as pyrazine, pyrazole, pyridazine, quinoxaline, purine, pyrrolidine, piperidine, 1-piperidine ethanol, 2-piperidine ethanol, morpholine, 4-methylmorpholine, piperazine, 1,4-dimethylpiperazine, 1,4-diazabicyclo[2.2.2]octane, and the like.

In addition, as the nitrogen-containing organic compound, a compound having an acid-labile group may be also used. Examples of the nitrogen-containing organic compound having an acid-labile group include N-(t-butoxycarbonyl)piperidine, N-(t-butoxycarbonyl)imidazole, N-(t-butoxycarbonyl)benzimidazole, N-(t-butoxycarbonyl)-2-phenylbenzimidazole, N-(t-butoxycarbonyl)di-n-octylamine, N-(t-butoxycarbonyl)diethanolamine, N-(t-butoxycarbonyl)dicyclohexylamine, N-(t-butoxycarbonyl)diphenylamine, tert-butyl-4-hydroxy-1-piperidine carboxylate, and the like.

Of these nitrogen-containing organic compounds, the nitrogen-containing compound (α), the nitrogen-containing compound (β), the nitrogen-containing heterocyclic compound, the nitrogen-containing organic compound having an acid-labile group, and the like are preferred.

Alternatively, a compound represented by the following formula (D1-0) may be also used as the acid diffusion control agent.

$$X^+Z^- \qquad (D1-0)$$

In the above formula (D1-0), $X^+$ is a cation represented by the following formula (D1-1) or (D1-2); and $Z^-$ is $OH^-$, an anion represented by the formula (D1-3): $R^{D1}$—$COO^-$ or an anion represented by the general formula (D1-4): $R^{D1}$—$SO_3^-$, wherein in the above formulae (D1-3) and (D1-4), $R^{D1}$ represents an unsubstituted or substituted alkyl group, alicyclic hydrocarbon group or aryl group.

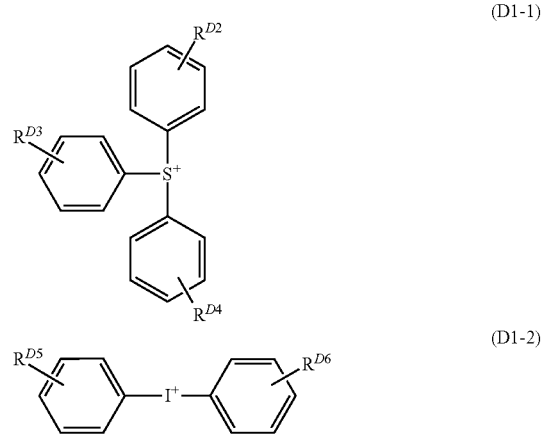

In the above formula (D1-1), $R^{D2}$ to $R^{D4}$ each independently represent a hydrogen atom, an alkyl group, an alkoxyl group, a hydroxyl group or a halogen atom. In the above formula (D1-2), $R^{D5}$ and $R^{D6}$ each independently represent a hydrogen atom, an alkyl group, an alkoxyl group, a hydroxyl group or a halogen atom.

The compound is used as an acid diffusion control agent that is degraded by exposure and lose acid diffusion controllability (hereinafter, may be also referred to as "photodegradable acid diffusion control agent"). Due to including the compound, an acid is diffused at sites exposed to light whereas diffusion of an acid is controlled at sites not exposed to light, thereby enabling a superior contrast between the site exposed to light and the site not exposed to light to be attained (i.e., enabling a boundary portion between the light-exposed site and the light-unexposed site to be clear). Therefore, in particular, LWR and MEEF of the radiation-sensitive resin composition of the embodiment of the present invention can be effectively improved.

$X^+$ $X^+$ in the above formula (D1-0) is a cation represented by the general formula (D1-1) or (D1-2) as described above. In addition, $R^{D2}$ to $R^{D4}$ in the general formula (D1-1) each independently represent a hydrogen atom, an alkyl group, an alkoxyl group, a hydroxyl group, or a halogen atom. Of these, due to having an effect of decreasing the solubility of the compound in the developer solution, $R^{D2}$ to $R^{D4}$ preferably represent a hydrogen atom, an alkyl group, an alkoxy group or a halogen atom. In addition, $R^{D5}$ and $R^{D6}$ in the general formula (D1-2) each independently represent a hydrogen atom, an alkyl group, an alkoxyl group, a hydroxyl group, or a halogen atom. Of these, a hydrogen atom, an alkyl group and a halogen atom are preferred.

$Z^-$ $Z^-$ in the above formula (D1-0) is $OH^-$, an anion represented by the general formula (D1-3): $R^{D1}$—$COO^-$, or an anion represented by the general formula (D1-4): $R^{D1}$—$SO_3^-$, wherein, $R^{D1}$ in the general formulae (D1-3) and (D1-4) is an unsubstituted or optionally substituted alkyl group, alicyclic hydrocarbon group or aryl group, and of these, an alicyclic hydrocarbon group or an aryl group is preferred due to having an effect of decreasing the solubility of the compound in the developer solution.

Examples of the unsubstituted or optionally substituted alkyl group include groups having one or more substituent such as e.g.: hydroxyalkyl groups having 1 to 4 carbon atoms such as a hydroxymethyl group, a 1-hydroxyethyl group, a 2-hydroxyethyl group, a 1-hydroxypropyl group, a 2-hydroxypropyl group, a 3-hydroxypropyl group, a 1-hydroxybutyl group, a 2-hydroxybutyl group, a 3-hydroxybutyl group and a 4-hydroxybutyl group; alkoxyl groups having 1 to 4 carbon atoms such as a methoxy group, an ethoxy group, a n-propoxy group, an i-propoxy group, a n-butoxy group, a 2-methylpropoxy group, a 1-methylpropoxy group and a t-butoxy group; a cyano group; cyanoalkyl groups having 2 to 5 carbon atoms such as a cyanomethyl group, a 2-cyanoethyl group, a 3-cyanopropyl group and a 4-cyanobutyl group, and the like. Of these, a hydroxymethyl group, a cyano group and a cyanomethyl group are preferred.

Examples of the unsubstituted or optionally substituted alicyclic hydrocarbon group include cycloalkane skeletons such as hydroxycyclopentane, hydroxycyclohexane and cyclohexanone; monovalent groups derived from an alicyclic hydrocarbon having a bridged alicyclic skeleton such as 1,7,7-trimethylbicyclo[2.2.1]heptan-2-one (camphor), and the like. Of these, groups derived from 1,7,7-trimethyl bicyclo[2.2.1]heptan-2-one are preferred.

Examples of the unsubstituted or optionally substituted aryl group include a phenyl group, a benzyl group, a phenylethyl group, a phenylpropyl group, a phenylcyclohexyl group, and the like, as well as groups derived by substituting these compounds with a hydroxyl group, a cyano group, etc., and the like. Of these, a phenyl group, a benzyl group and a phenylcyclohexyl group are preferred.

It is to be noted that Z⁻ in the general formula (D1-0) is preferably an anion represented by the following formula (1a) (i.e., an anion represented by the general formula (D1-3) in which $R^{D1}$ represents a phenyl group) or an anion represented by the following formula (1b) (i.e., an anion represented by the general formula (D1-4) in which $R^{D1}$ represents a group derived from 1,7,7-trimethyl bicyclo[2.2.1]heptan-2-one).

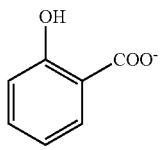

(1a)

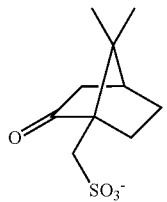

(1b)

The photodegradable acid diffusion control agent is one represented by the general formula (D1-0), and specifically, a sulfonium salt compound or an iodonium salt compound that satisfies the aforementioned requirements.

Examples of the sulfonium salt compound include triphenylsulfonium hydroxide, triphenylsulfonium acetate, triphenylsulfonium salicylate, diphenyl-4-hydroxyphenylsulfonium hydroxide, diphenyl-4-hydroxyphenylsulfonium acetate, diphenyl-4-hydroxyphenylsulfonium salicylate, triphenylsulfonium 10-camphorsulfonate, 4-t-butoxyphenyl-diphenylsulfonium 10-camphorsulfonate, and the like. It is to be noted that these sulfonium salt compounds may be used either alone or in combination of two or more thereof.

Moreover, examples of the iodonium salt compound include bis(4-t-butylphenyl)iodonium hydroxide, bis(4-t-butylphenyl)iodonium acetate, bis(4-t-butylphenyl)iodonium hydroxide, bis(4-t-butylphenyl)iodonium acetate, bis(4-t-butylphenyl)iodonium salicylate, 4-t-butylphenyl-4-hydroxyphenyliodonium hydroxide, 4-t-butylphenyl-4-hydroxyphenyliodonium acetate, 4-t-butylphenyl-4-hydroxyphenyliodonium salicylate, bis(4-t-butylphenyl)iodonium 10-camphorsulfonate, diphenyliodonium 10-camphorsulfonate, and the like. It is to be noted that iodonium salt compounds may be used either alone or in combination of two or more thereof.

The acid diffusion control agent may be used either alone, or as a mixture of two or more types thereof.

The amount of the acid diffusion control agent (D) blended is preferably 0.1 parts by mass to 25 parts by mass, more preferably 1 parts by mass to 20 parts by mass, and particularly preferably 3 parts by mass to 16 parts by mass with respect to 100 parts by mass of the polymer (B). In this case, when the amount of the acid diffusion control agent blended is no less than 0.1 parts by mass, deterioration of the pattern configuration and/or dimension fidelity depending on the process conditions can be inhibited, whereas when the amount is no greater than 25 parts by mass, the sensitivity and/or alkali developability as a resist can be further improved.

(E) Lactone Compound

The lactone compound (E) has an effect of efficiently segregating the polymer (C) on the surface of the resist film, the polymer (C) having an action of allowing water repellency to be expressed on the surface of the resist film in liquid immersion lithography. Thus, due to including the lactone compound (E) when the polymer (C) is used, the amount of the polymer (C) added can be reduced. Therefore, elution of a component from a resist film to a liquid for liquid immersion can be inhibited without impairing basic characteristics as a resist, and water repellency of the surface of the resist film that inhibits defects derived from the liquid immersion such as watermark defects can be maintained as a result of no remaining of droplets even if liquid immersion lithography is carried out by high-speed scanning.

Specific examples of the lactone compound (E) include γ-butyrolactone, valerolactone, mevalonic lactone, norbornanelactone and the like, and γ-butyrolactone is preferred.

The photoresist composition in the embodiment of the present invention may contain the lactone compound (E) of only one type, or two or more types thereof.

In the photoresist composition of the embodiment of the present invention, the content of the lactone compound (E) in the radiation-sensitive resin composition is typically 30 to 200 parts by mass, and more preferably 50 to 150 parts by mass with respect to 100 parts by mass of the polymer (B). When the content of the lactone compound (E) is too small, water repellency of the surface of the resist film cannot be sufficiently attained in adding a small amount of the polymer (C). On the other hand, when the content is excessive, basic performances of the resist and pattern configuration after the development may be significantly deteriorated.

Other Additives

To the radiation-sensitive resin composition of the embodiment of the present invention may be added other component(s) in addition to the components (A) to (E). The other component is exemplified by other radiation-sensitive compound, a dissolution control agent, a surfactant, a sensitizing agent, and the like.

Other Radiation-Sensitive Compound

In the radiation-sensitive resin composition of the embodiment of the present invention, at least one compound other than the compound (A) (hereinafter, may be referred to as "other radiation-sensitive compound") may be used in combination as a radiation-sensitive compound (radiation-sensitive acid generating agent).

Examples of the other radiation-sensitive compound include onium salt compounds, sulfone compounds, sulfonic acid ester compounds, sulfonimide compounds, diazomethane compounds, disulfonylmethane compounds, oximesulfonate compounds, hydrazine sulfonate compounds, and the like.

These compounds are exemplified by compounds described in WO2009/051088, paragraph nos. [0086] to [0113].

Of these other radiation-sensitive compounds, one, or two or more compounds from the group consisting of an onium salt compound, a sulfonimide compound and a diazomethane compound are preferred.

Examples of particularly preferable other radiation-sensitive compound include diphenyliodonium trifluoromethanesulfonate, diphenyliodonium nonafluoro-n-butanesulfonate, diphenyliodonium p-toluenesulfonate, diphenyliodonium 10-camphorsulfonate, diphenyliodonium 2-trifluoromethylbenzenesulfonate, diphenyliodonium 4-trifluoromethylbenzenesulfonate, diphenyliodonium 2,4-difluorobenzenesulfonate, diphenyliodonium 1,1,2,2-tetrafluoro-2-(norbornan-2-yl)ethanesulfonate, diphenyliodonium 2-(5-t-butoxycarbonyloxybicyclo[2.2.1]heptan-2-yl)-1,1,2,2-tetrafluoroethanesulfonate, diphenyliodonium 2-(6-t-butoxycarbonyloxybicyclo[2.2.1]heptan-2-yl)-1,1,2,2-tetrafluoroethanesulfonate, diphenyliodonium 1,1-difluoro-2-(bicyclo[2.2.1]heptan-2-yl)ethanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium p-toluenesulfonate, bis(4-t-butylphenyl)iodonium 10-camphorsulfonate, bis(4-t-butylphenyl)iodonium 2-trifluoromethylbenzenesulfonate, bis(4-t-butylphenyl)iodonium 4-trifluoromethylbenzenesulfonate, bis(4-t-butylphenyl)iodonium 2,4-difluorobenzenesulfonate, bis(4-t-butylphenyl)iodonium 1,1,2,2-tetrafluoro-2-(norbornan-2-yl)ethanesulfonate, bis(4-t-butylphenyl)iodonium 1,1-difluoro-2-(bicyclo[2.2.1]heptan-2-yl)ethanesulfonate, triphenylsulfonium trifluoromethanesulfonate, triphenylsulfonium nonafluoro-n-butanesulfonate, triphenylsulfonium p-toluenesulfonate, triphenylsulfonium 10-camphorsulfonate, triphenylsulfonium 2-trifluoromethylbenzenesulfonate, triphenylsulfonium 4-trifluoromethylbenzenesulfonate, triphenylsulfonium 2,4-difluorobenzenesulfonate, triphenylsulfonium 1,1,2,2-tetrafluoro-2-(norbornan-2-yl)ethanesulfonate, triphenylsulfonium 2-(5-t-butoxycarbonyloxybicyclo[2.2.1]heptan-2-yl)-1,1,2,2-tetrafluoroethanesulfonate, triphenylsulfonium 2-(6-t-butoxycarbonyloxybicyclo[2.2.1]heptan-2-yl)-1,1,2,2-tetrafluoroethanesulfonate, triphenylsulfonium 2-(5-pivaloyloxybicyclo[2.2.1]heptan-2-yl)-1,1,2,2-tetrafluoroethanesulfonate, triphenylsulfonium 2-(6-pivaloyloxybicyclo[2.2.1]heptan-2-yl)-1,1,2,2-tetrafluoroethanesulfonate, triphenylsulfonium 2-(5-hydroxybicyclo[2.2.1]heptan-2-yl)-1,1,2,2-tetrafluoroethanesulfonate, triphenylsulfonium 2-(6-hydroxybicyclo[2.2.1]heptan-2-yl)-1,1,2,2-tetrafluoroethanesulfonate, triphenylsulfonium 2-(5-methanesulfonyloxybicyclo[2.2.1]heptan-2-yl)-1,1,2,2-tetrafluoroethanesulfonate, triphenylsulfonium 2-(6-methanesulfonyloxybicyclo[2.2.1]heptan-2-yl)-1,1,2,2-tetrafluoroethanesulfonate, triphenylsulfonium 2-(5-i-propane sulfonyloxybicyclo[2.2.1]heptan-2-yl)-1,1,2,2-tetrafluoroethanesulfonate, triphenylsulfonium 2-(6-i-propane sulfonyloxybicyclo[2.2.1]heptan-2-yl)-1,1,2,2-tetrafluoroethanesulfonate, triphenylsulfonium 2-(5-n-hexanesulfonyloxybicyclo[2.2.1]heptan-2-yl)-1,1,2,2-tetrafluoroethanesulfonate, triphenylsulfonium 2-(6-n-hexanesulfonyloxybicyclo[2.2.1]heptan-2-yl)-1,1,2,2-tetrafluoroethanesulfonate, triphenylsulfonium 2-(5-oxobicyclo[2.2.1]heptan-2-yl)-1,1,2,2-tetrafluoroethanesulfonate, triphenylsulfonium 2-(6-oxobicyclo[2.2.1]heptan-2-yl)-1,1,2,2-tetrafluoroethanesulfonate, triphenylsulfonium 1,1-difluoro-2-(bicyclo[2.2.1]heptan-2-yl)ethanesulfonate, 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-1-yl)tetrahydrothiophenium 1,1,2,2-tetrafluoro-2-(norbornan-2-yl)ethanesulfonate, 1-(4-n-butoxynaphthalen-1-yl)tetrahydrothiophenium 2-(5-t-butoxycarbonyloxybicyclo[2.2.1]heptan-2-yl)-1,1,2,2-tetrafluoroethanesulfonate, 1-(4-n-butoxynaphthalen-1-yl)tetrahydrothiophenium 2-(6-t-butoxycarbonyloxybicyclo[2.2.1]heptan-2-yl)-1,1,2,2-tetrafluoroethanesulfonate, 1-(4-n-butoxynaphthalen-1-yl)tetrahydrothiophenium 1,1-difluoro-2-(bicyclo[2.2.1]heptan-2-yl)ethanesulfonate, N-(trifluoromethanesulfonyloxy)succinimide, N-(10-camphorsulfonyloxy)succinimide, N-[(5-methyl-5-carboxymethylbicyclo[2.2.1]heptan-2-yl)sulfonyloxy]succinimide, N-(trifluoromethanesulfonyloxy)bicyclo[2.2.1]hept-5-ene-2,3-dicarboxylmide, N-(nonafluoro-n-butanesulfonyloxy)bicyclo[2.2.1]hept-5-ene-2,3-dicarboxylmide, N-[1,1,2,2-tetrafluoro-2-(norbornan-2-yl)ethanesulfonyloxy]bicyclo[2.2.1]hept-5-ene-2,3-dicarboxyimide, N-(10-camphorsulfonyloxy)bicyclo[2.2.1]hept-5-ene-2,3-dicarboxylmide, N-[2-(5-oxobicyclo[2.2.1]heptan-2-yl)-1,1,2,2-tetrafluoroethanesulfonyloxy]bicyclo[2.2.1]hept-5-ene-2,3-dicarboxylmide, N-[2-(6-oxobicyclo[2.2.1]heptan-2-yl)-1,1,2,2-tetrafluoroethanesulfonyloxy]bicyclo[2.2.1]hept-5-ene-2,3-dicarboxylmide, N-[1,1-difluoro-2-(bicyclo[2.2.1]heptan-2-yl)ethanesulfonyloxy]bicyclo[2.2.1]hept-5-ene-2,3-dicarboxylmide, bis(cyclohexanesulfonyl)diazomethane, bis(t-butylsulfonyl)diazomethane, bis(1,4-dioxaspiro[4.5]decane-7-sulfonyl)diazomethane, and the like.

The proportion of the other radiation-sensitive compound used may be appropriately selected in accordance with the type of the other radiation-sensitive compound, and is typically no greater than 95 parts by mass, preferably no greater than 90 parts by mass, and more preferably no greater than 80 parts by mass with respect to 100 parts by mass of the total of the compound (A) and the other radiation-sensitive compound. In this case, when the proportion of the other radiation-sensitive compound used is excessive, desired effects of the present invention may be impaired.

Dissolution Control Agent

A dissolution control agent having a property that solubility in an alkaline developer is enhanced by an action of an acid may be blended in the radiation-sensitive resin composition of the embodiment of the present invention.

Such a dissolution control agent is exemplified by a compound having an acidic functional group such as a phenolic hydroxyl group, a carboxyl group or a sulfonic acid group, as well as a compound obtained by substituting a hydrogen atom of the acidic functional group in the above-described compound with an acid-labile group, and the like.

The dissolution control agent may be either a low molecular compound or a high molecular compound, and as a high molecular dissolution control agent in a radiation-sensitive negative resin composition, for example, an acid-labile group-containing polymer in the positive radiation-sensitive resin composition may be used. The dissolution control agent may be used either alone, or as a mixture of two or more thereof.

The content of the dissolution control agent blended is typically no greater than 50 parts by mass, and preferably no greater than 20 parts by mass with respect to 100 parts by mass of the component of the polymer (B).

Surfactant

A surfactant having an effect of improving coating properties, striation, developability and the like of the radiation-sensitive resin composition may be blended in the radiation-sensitive resin composition of the embodiment of the present invention.

As such a surfactant, any of an anionic, cationic, nonionic or amphoteric surfactant may be used, and a nonionic surfactant is preferably used.

Examples of the nonionic surfactant include polyoxyethylene higher alkyl ethers, polyoxyethylene higher alkylphenyl ethers, higher aliphatic acid diesters of polyethylene glycol, as well as each series of the following trade names, "KP" (manufactured by Shin-Etsu Chemical Co., Ltd.), "Polyflow" (manufactured by Kyoeisha Chemical Co., Ltd.), "EFTOP" (manufactured by Mitsubishi Materials Electronic Chemicals Co., Ltd. (formerly, JEMCO Inc.)), "MEGAFACE" (manufactured by Dainippon Ink and Chemicals, Incorporated), "Fluorad" (manufactured by Sumitomo 3M Limited), "AsahiGuard" and "Surflon" (manufactured by Asahi Glass Co., Ltd.), and the like. The surfactant may be used either alone, or as a mixture of two or more thereof.

The amount of the surfactant blended is typically no greater than 2 parts by mass, and preferably no greater than 1.5 parts by mass with respect to 100 parts by mass of the component of the polymer (B) as the active ingredient of the surfactant.

Sensitizing Agent

The radiation-sensitive resin composition of the embodiment of the present invention may also contain a sensitizing agent capable of absorbing energy of a radioactive ray, and transmitting the energy to a radiation-sensitive acid generator, thereby increasing the amount of the acid produced to improve apparent sensitivity of the radiation-sensitive resin composition. Such a sensitizer is exemplified by acetophenones, benzophenones, naphthalenes, biacetyl, eosine, rose bengal, pyrenes, anthracenes, phenothiazines, and the like. These sensitizing agents may be used either alone, or as a mixture of two or more thereof.

The amount of the sensitizing agent blended is typically no greater than 50 parts by mass, and preferably no greater than 30 parts by mass with respect to 100 parts by mass of the component of the polymer (B).

Furthermore, the radiation-sensitive resin composition of the embodiment of the present invention may contain additives other than those described in the foregoing such as, for example, a dye, a pigment, an adhesion promoter, a halation inhibitor, a storage stabilizer, a defoaming agent and a shape improving agent, specifically 4-hydroxy-4'-methylchalcone, or the like as needed within the range not to impair the effects of the present invention. In this case, due to containing a dye or a pigment, a latent image of the light-exposed site can be visualized to mitigate the influences from halation in the exposure. Moreover, due to containing an adhesion promoter, adhesiveness to the substrate can be improved.

Preparation Method of Radiation-Sensitive Resin Composition

The radiation-sensitive resin composition of the embodiment of the present invention is prepared in the form of a composition solution by generally dissolving each component in a solvent in use to give a homogenous solution, and thereafter filtering through, for example, a filter having a pore size of about 0.2 μm or the like as needed.

The solvent is exemplified by ethers, esters, ether esters, ketones, ketone esters, amides, amide esters, lactams, (halogenated) hydrocarbons, and the like. More specifically, examples of the solvent include ethylene glycol monoalkyl ethers, diethylene glycol dialkyl ethers, propylene glycol monoalkyl ethers, propylene glycol dialkyl ethers, ethylene glycol monoalkyl ether acetates, propylene glycol monoalkyl ether acetates, acyclic or cyclic ketones, ester acetates, hydroxy ester acetates, alkoxy ester acetates, aceto ester acetates, propionic acid esters, lactic acid esters, other substituted propionic acid esters, (substituted) butyric acid esters, pyruvic acid esters, N,N-dialkylformamides, N,N-dialkylacetamides, N-alkylpyrrolidones, (halogenated) aliphatic hydrocarbons, (halogenated) aromatic hydrocarbons, and the like.

Specific examples of the solvent include those described in WO2009/051088, paragraph no. [0202].

Of these solvents, propylene glycol monoalkyl ether acetates, acyclic or cyclic ketones, lactic acid esters, 3-alkoxypropionic acid esters and the like are preferred in that favorable film intra-plane uniformity can be secured in the coating. Of these, propylene glycol monoalkyl ether acetates and cyclic ketones are more preferred. The solvent may be used either alone, or as a mixture of two or more thereof.

In addition, other solvent may be used as needed together with the solvent described above, such as a solvent having a high boiling point like e.g., benzylethyl ether, di-n-hexyl ether, diethylene glycol monomethyl ether, diethylene glycol monoethyl ether, acetonyl acetone, isophorone, caproic acid, caprylic acid, 1-octanol, 1-nonanol, benzyl alcohol, benzyl acetate, ethyl benzoate, diethyl oxalate, diethyl maleate, ethylene carbonate, propylene carbonate, ethylene glycol monophenyl ether acetate, or the like.

The other solvent may be used either alone, or as a mixture of two or more thereof. The proportion of the other solvent used is typically no greater than 50% by mass, and preferably no greater than 30% by mass with respect to the total of the solvent.

The total amount of the solvent used is an amount that makes the total solid content of the radiation-sensitive composition solution be typically 5 to 50% by mass, preferably 10 to 50% by mass, more preferably 10 to 40% by mass, particularly preferably 10 to 30% by mass, and in particular 10 to 25% by mass. When the total solid content of the solution falls within the above range, favorable film intra-plane uniformity can be secured in the coating.

Formation of Resist Pattern

When a resist pattern is formed from the radiation-sensitive resin composition of the embodiment of the present invention, a solution of the composition prepared as described above is applied onto a substrate such as, for example, a silicon wafer or a wafer covered with aluminum by an appropriate coating means such as spin-coating, cast coating or roll coating to form a resist coating film. Thereafter, after a heating treatment (hereinafter, may be referred to as "PB") is carried out beforehand as the case may be, the resist coating film is exposed through a predetermined mask pattern.

The radioactive ray which may be used in the exposure is exemplified by far ultraviolet rays such as a bright line spectrum in a mercury lamp (wavelength: 254 nm), a KrF excimer laser (wavelength: 248 nm), an ArF excimer laser (wavelength: 193 nm), an $F_2$ excimer laser (wavelength: 157 nm), and EUV light (wavelength: 13 nm, etc.), as well as X-rays such as synchrotron radioactive rays, charged particle-rays such as electron beams, and the like. The radioactive ray is preferably a far ultraviolet ray and a charged particle-ray. Particularly preferably, the radioactive ray is a KrF excimer laser (wavelength: 248 nm), an ArF excimer laser (wavelength: 193 nm), an $F_2$ excimer laser (wavelength: 157 nm) and electron beams, in accordance with the type of the radiation-sensitive acid generating agent employed. Alternatively, a liquid for liquid immersion lithography may be placed on a resist coating film, and the resist coating film can be exposed through the liquid for liquid immersion lithography (liquid immersion lithography).

In addition, conditions for exposure such as radiation dose may be determined ad libitum depending on the compositional formulation of the radiation-sensitive resin composition, the type of the additive, and the like. Additionally, in forming the resist pattern, it is preferable to carry out a heat treatment after the exposure (hereinafter, may be referred to as "PEB") in light of improvement of apparent sensitivity of the resist. Heating conditions of the PEB may vary depending on the compositional formulation of the radiation-sensitive resin composition, the type of the additive, and the like, the temperature is typically 30 to 200° C., and preferably 50 to 150° C.

Thereafter, the exposed resist coating film is developed with an alkaline developer solution to form a predetermined positive or negative resist pattern.

As the alkaline developer solution, for example, an aqueous alkaline solution prepared by dissolving one or more alkaline compounds such as alkali metal hydroxide, ammonia water, alkylamines, alkanolamines, heterocyclic amines, tetraalkylammonium hydroxides, choline, 1,8-diazabicyclo[5.4.0]-7-undecene, and 1,5-diazabicyclo[4.3.0]-5-nonene may be used. Particularly preferred alkaline developer solution is an aqueous solution of tetraalkylammonium hydroxides.

The concentration of the aqueous alkaline solution is preferably no greater than 10% by mass, more preferably 1 to 10% by mass, and particularly preferably 2 to 5% by mass. In this instance, when the concentration of the aqueous alkaline solution is no greater than 10% by mass, dissolution at a light-unexposed site (in the case of positive type) at a light-exposed site (in the case of negative type) in the alkaline developer can be suppressed.

In addition, an appropriate amount of a surfactant and the like may be preferably added to a developer solution consisting of the aqueous alkaline solution, whereby wettability of the alkaline developer solution with respect to the resist coating film can be improved. Note that after the development carried out with the developer solution constituted with the aqueous alkaline solution, in general, washing with water and drying will follow.

Radiation-Sensitive Acid Generating Agent

The radiation-sensitive acid generating agent of the embodiment of the present invention included the compound (A) described in the foregoing. The radiation-sensitive acid generating agent of the embodiment of the present invention is suitably used for the radiation-sensitive resin composition of the embodiment of the present invention. The radiation-sensitive acid generating agent may be either the compound (A) alone, or a combination with the other radiation-sensitive compound, and is preferably the compound (A) alone. Details of the compound (A) are as described above.

EXAMPLES

Hereinafter, the present invention will be specifically explained by way of Examples, but the present invention is not limited to these Examples. It is to be noted that the "%" in Examples and Comparative Examples is on a molar basis unless otherwise stated particularly. Furthermore, methods for the determination of various types of physical property values, and evaluation methods of various characteristics are shown below.

Conditions of Evaluations

With respect to Examples and Comparative Examples, positive resist patterns were formed according to the pattern-forming method (P-1) or (P-2) described below, and each evaluation was made.

Pattern-Forming Method (P-1)

On a 12-inch silicon wafer having an underlayer antireflective film ("ARC66", manufactured by Nissan Chemical Industries, Ltd.) provided thereon, a coating film having a film thickness of 75 nm was provided by a radiation-sensitive resin composition, and thereafter subjected to PB (prebaking) at a temperature shown in Table 1 for 60 sec. Next, the coating film was exposed through a mask pattern using an ArF excimer laser immersion Scanner ("NSR S610C", manufactured by NIKON Corporation) under a condition involving an NA of 1.3, a ratio of 0.800 and Annular. After the exposure, post-baking (PEB) was carried out at 95° C. for 60 sec. Thereafter, the coating film was developed with a 2.38% by mass aqueous tetramethylammonium hydroxide solution and washed with water, followed by drying to form a positive type resist pattern.

Pattern-Forming Method (P-2)

On a 12-inch silicon wafer having an underlayer antireflective film ("ARC66", manufactured by Nissan Chemical Industries, Ltd.) provided thereon, a coating film having a film thickness of 75 nm was provided by a radiation-sensitive resin composition, and thereafter subjected to PB at a temperature shown in Table 1 for 60 sec. Next, a composition for forming an upper layer film described in Example 1 of WO 2008/047678 was spin-coated on the coating film formed, and PB was carried out at 90° C. for 60 sec to form a coating film having a film thickness of 90 nm. This coating film was exposed through a mask pattern using an ArF excimer laser immersion Scanner ("NSR S610C", manufactured by NIKON Corporation) under a condition involving an NA of 1.3, a ratio of 0.800 and Annular. After the exposure, post-baking (PEB) was carried out at at a temperature shown in Table 1 for 60 sec. Thereafter, the coating film was developed with a 2.38% by mass aqueous tetramethylammonium hydroxide solution and washed with water, followed by drying to form a positive type resist pattern.

MEEF

An exposure dose at which a line-and-space (LS) pattern having a line width of 50 nm was formed by exposing through a 1 L/1 S mask pattern with a target size of 50 nm under the condition of evaluation described above was defined as "optimal exposure dose". Then an LS pattern having a pitch of 100 nm was formed at this optimal exposure dose using each mask pattern with a target size of the line width of 46 nm, 48 nm, 50 nm, 52 nm or 54 nm, and the line width formed on the resist film was measured with an SEM for line-width measurement (CG4000, manufactured by Hitachi, Ltd.).

In this procedure, the line width (nm) formed on the resist film using each mask pattern was plotted along the ordinate with respect to the target size (nm) along the abscissa, and the slope of the resulting straight line was determined as MEEF performance.

LWR

An exposure dose at which a resist pattern having a line width of 50 nm was formed by exposing through a 1 L/1.8 S mask pattern with a target size of 50 nm under the condition of evaluation described above was defined as "optimal exposure dose". In the observation of the pattern with a line width of 50 nm obtained at the optimal exposure dose, line widths at arbitrary ten points were measured when observed from above the pattern using an SEM for critical dimension measurement: CG4000 manufactured by Hitachi, Ltd., and the variance of measurements expressed as a value in terms of the 3 Sigma was defined as "LWR". The lower LWR value indicates more favorable linearity of the pattern.

Minimum Collapse Dimension

The exposure was carried out through a 1 L/1.8 S mask pattern with a target size of 50 nm under the condition of evaluation described above while changing the exposure dose by 1 mJ. The line width of the pattern formed at an exposure dose less than the exposure dose at which the line collapse occurred by 1 mJ was measured with an SEM for critical dimension measurement (model "CG4000" manufactured by Hitachi, Ltd.,). The line width measured was defined as a minimum collapse dimension.

Note that the smaller value thus determined indicates more superior resistance to pattern collapse.

Synthesis Example 1

Synthesis of Polymer (B)

A monomer solution was prepared by dissolving 31.63 g (35 mol %) of a compound (S-1) described below, 49.60 g (45 mol %) of a compound (S-3) described below, 6.45 g (10 mol %) of a compound (S-4) described below in 200 g of 2-butanone and further charging thereto 8.14 g of 2,2'-azobis(2-methylpropionitrile). A 1,000 mL three-neck flask which had been charged with 12.32 g (10 mol %) of compound (S-2) described below and 100 g of 2-butanone was purged with nitrogen for 30 min. After the nitrogen purge, the reaction vessel was heated to 80° C. with stirring, and the monomer solution prepared beforehand was added dropwise thereto over 3 hrs using a dripping funnel. A time point at which the dropwise addition was started was defined as a polymerization starting time, and the polymerization reaction was performed for 6 hrs. After the completion of the polymerization, the polymerization solution was cooled to no higher than 30° C. by water-cooling, and charged into 4,000 g of methanol. The white powder thus precipitated was filtered off. The white powder obtained by filtration was dispersed in 400 g of methanol to give a slurry state, followed by washing and filtration. Such an operation was repeated twice, and thereafter vacuum dried at 50° C. for 17 hrs to obtain a copolymer (resin (B-1)) as a white powder. The copolymer had an Mw of 4,300 and Mw/Mn of 1.30. As a result of a $^{13}$C-NMR analysis, the copolymer had a content of each of the structural units derived from the compound (S-1), the compound (S-2), the compound (S-3) and the compound (S-4) of 35.6: 8.9: 46.2: 9.3 (mol %). The copolymer is designated as polymer (B-1).

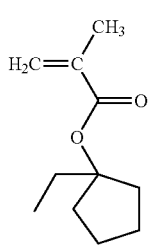
(S-1)

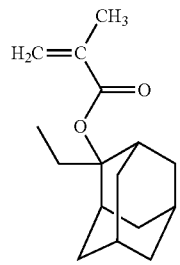
(S-2)

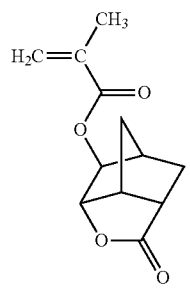
(S-3)

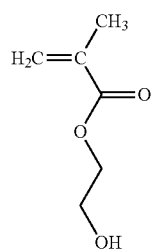
(S-4)

Synthesis Example 2

Synthesis of Polymer (C)

A monomer solution was prepared by dissolving 37.41 g (40 mol %) of a compound (S-5) described below and 62.59 g (60 mol %) of a compound (S-6) described below in 100 g of 2-butanone and further charging thereto 4.79 g of 2,2'-azobis(2-methylpropionitrile). A 1,000 mL three-neck flask which had been charged with 100 g of 2-butanone was purged with nitrogen for 30 min. After the nitrogen-purge, the reaction vessel was heated to 80° C. with stirring, and the monomer solution prepared beforehand was added dropwise thereto over 3 hrs using a dripping funnel. A time point at which the dropwise addition was started was defined as a polymerization starting time, and the polymerization reaction was performed for 6 hrs. After the completion of the polymerization, 150 g of 2-butanone was removed in vacuo from the polymerization solution. After cooling to no higher than 30° C., the polymerization solution was charged into a mixed solvent of 900 g of methanol and 100 g of ultra pure water. The white powder thus precipitated was filtered off. The white powder obtained by filtration was dispersed in 100 g of methanol to give a slurry state, followed by washing and filtration. Such an operation was repeated twice. The resultant white powder was dried in vacuo at 50° C. for 17 hrs to give a copolymer (78 g, yield: 78%). The copolymer had an Mw of 6,920 and Mw/Mn of 1.592. As a result of a $^{13}$C-NMR analysis, the copolymer had a content of each of the structural units derived from the compound (S-5) and the compound (S-6) of 40.8: 59.2 (mol %). The fluorine content was 9.6% by mass. The copolymer is designated as polymer (C-1).

(s-5)

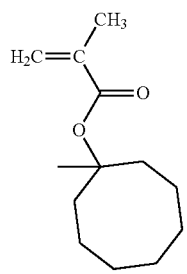

(s-6)

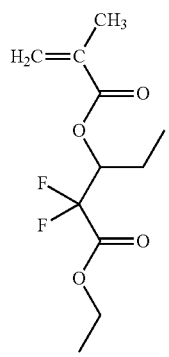

Preparation of Radiation-Sensitive Resin Composition

Components other than the polymer (B) and the polymer (C) of the radiation-sensitive resin composition used in each Example and Comparative Example are as follows. Some of the components are shown together with the chemical formula thereof.

Compound (A)

(A-1): Compound Represented by the Following Formula

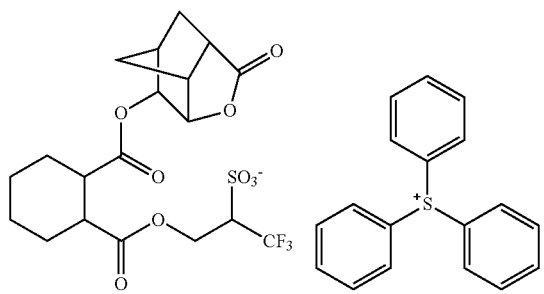

(A-2): Compound Represented by the Following Formula

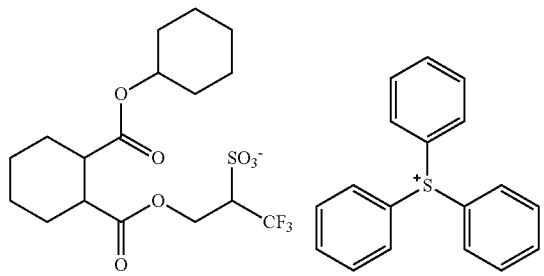

(A-3): Compound Represented by the Following Formula

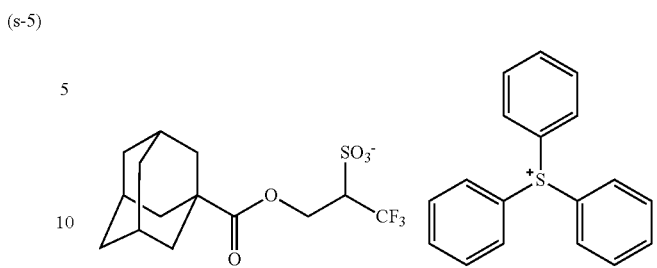

(A-4): Compound Represented by the Following Formula

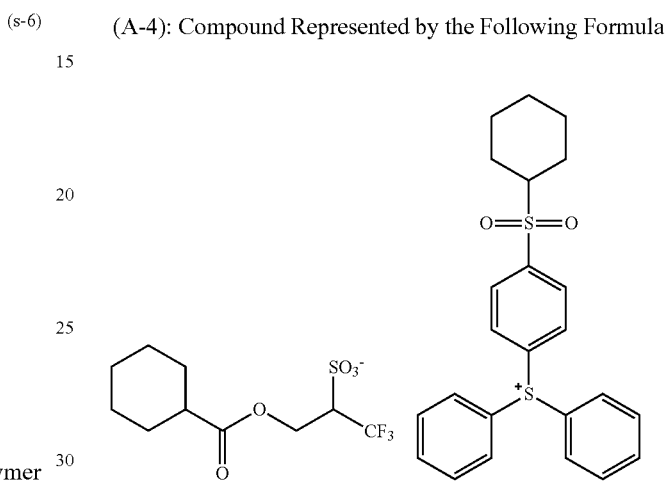

(a-1) triphenylsulfonium 4-(1-adamantanecarbonyloxy)-1,1,2,2-tetrafluorobutanesulfonate (compound represented by the following formula)

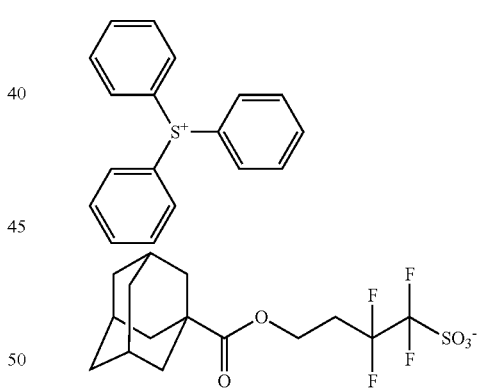

Acid Diffusion Control Agent (D)

(D-1) triphenylsulfonium 2-hydroxybenzoate (compound represented by the following formula)

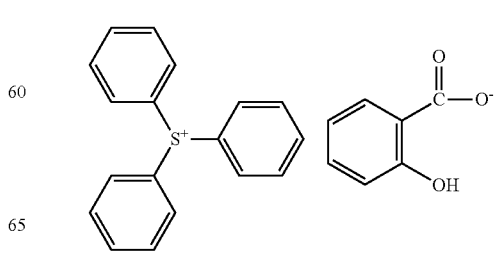

(D-2) tert-butyl-4-hydroxy-1-piperidine carboxylate (compound represented by the following formula)

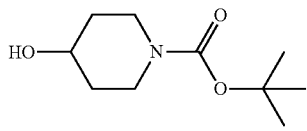

Lactone Compound (E)
(E-1) γ-butyrolactone
Solvent (F)
(F-1) Propylene Glycol Methyl Ether Acetate
(F-2) Cyclohexanone Example 1

The compound (A-1) in an amount of 13 parts by mass as the compound (A) (i.e., radiation-sensitive acid generating agent), 100 parts by mass of the polymer (B-1) as the polymer (B), 3 parts by mass of the polymer (C-1) as the polymer (C), 13 parts by mass of (D-1) as the acid diffusion control agent (D), 200 parts by mass of (G-1) as the lactone compound (E), and 1,980 parts by mass of (F-1) and 848 parts by mass of (F-2) as the solvent (F) were added and then the components were mixed to give a homogenous solution. Thereafter, the solution was filtrated through a membrane filter having a pore size of 200 nm to prepare a positive type radiation-sensitive composition (concentration of total solid contents: about 4%). Each composition thus obtained was evaluated on MEEF, LWR and Minimum collapse dimension under the conditions of evaluations described above in which the pattern-forming method (P-2) described above was employed. The results are shown in Table 1 all together.

Examples 2 to 10, and Comparative Examples 1 to 4

Positive type radiation-sensitive resin compositions were prepared in a similar manner to Example 1 except that the types and the amounts (parts by mass) of the compound (A), the polymer (B), the polymer (C), the acid diffusion control agent (D) and the lactone compound (E) were as shown in Table 1. The results of each evaluation are shown in Table 1 together with. It is to be noted that in the conditions of evaluations for Examples 1 to 5, and Comparative Examples 1 and 2, the aforementioned pattern-forming method (P-2) was employed, whereas in the conditions of evaluations for Examples 6 to 10, and Comparative Examples 3 and 4, the aforementioned pattern-forming method (P-1) was employed.

TABLE 1

| | (A) Compound | | (B) | (C) | (D) Acid diffusion control agent | | (E) Lactone | | | | | Minimum collapse |
|---|---|---|---|---|---|---|---|---|---|---|---|---|
| | designation of type | amount blended | Polymer (B-1) | Polymer (C-1) | designation of type | amount blended | compound (E-1) | PB (°C.) | PEB (°C.) | MEEF | LWR (nm) | dimension (nm) |
| Example 1 | A-1 | 13 | 100 | 3 | D-1 | 13 | 200 | 100 | 110 | 2.8 | 3.8 | 29 |
| Example 2 | A-1 | 12 | 100 | 3 | D-2 | 6 | 200 | 110 | 105 | 2.9 | 3.8 | 30 |
| Example 3 | A-2 | 13 | 100 | 3 | D-1 | 13 | 200 | 100 | 110 | 2.8 | 3.6 | 29 |
| Example 4 | A-3 | 13 | 100 | 3 | D-1 | 13 | 200 | 100 | 110 | 2.9 | 3.7 | 29 |
| Example 5 | A-4 | 13 | 100 | 3 | D-1 | 13 | 200 | 100 | 110 | 2.7 | 3.7 | 28 |
| Comparative Example 1 | a-1 | 13 | 100 | 3 | D-1 | 13 | 200 | 100 | 110 | 3.6 | 4.6 | 39 |
| Comparative Example 2 | a-1 | 12 | 100 | 3 | D-2 | 6 | 200 | 110 | 105 | 3.6 | 4.8 | 39 |
| Example 6 | A-1 | 13 | 100 | — | D-1 | 13 | — | 100 | 110 | 2.8 | 4 | 27 |
| Example 7 | A-1 | 12 | 100 | — | D-2 | 6 | — | 110 | 105 | 2.9 | 4.2 | 28 |
| Example 8 | A-2 | 13 | 100 | — | D-1 | 13 | — | 100 | 110 | 2.8 | 3.9 | 28 |
| Example 9 | A-3 | 13 | 100 | — | D-1 | 13 | — | 100 | 110 | 2.7 | 4 | 29 |
| Example 10 | A-4 | 13 | 100 | — | D-1 | 13 | — | 100 | 110 | 2.7 | 3.9 | 29 |
| Comparative Example 3 | a-1 | 13 | 100 | — | D-1 | 13 | — | 100 | 110 | 3.5 | 5.8 | 40 |
| Comparative Example 4 | a-1 | 12 | 100 | — | D-2 | 6 | — | 110 | 105 | 3.5 | 5.9 | 41 |

Note:
"—" indicating the addition of no component

As shown in Table 1, Examples and Comparative Examples verified that by using the radiation-sensitive resin composition of the embodiment of the present invention, LWR and minimum collapse dimension can be improved, and also favorable coordination with MEEF can be achieved.

As explained in the foregoing, the radiation-sensitive resin composition of the embodiment of the present invention is capable of forming a chemically amplified resist film that is favorable in resistance to pattern collapse after development, LWR and MEEF, and superior in coordination thereof. Therefore, the radiation-sensitive resin composition can be suitably used in the field of resists.

Obviously, numerous modifications and variations of the present invention are possible in light of the above teachings. It is therefore to be understood that within the scope of the appended claims, the invention may be practiced otherwise than as specifically described herein.

The invention claimed is:
1. A radiation-sensitive resin composition comprising:
a compound represented by a formula (1); and
a base polymer

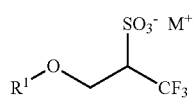

wherein, in the formula (1), $R^1$ is a group represented by a formula (a1); and $M^+$ represents a radiation-degradable monovalent cation,

wherein, in the formula (a1), $R^2$ represents a alicyclic hydrocarbon group having 3 to 30 carbon atoms or a heterocyclic group having 3 to 30 ring atoms; $R^3$ represents a divalent hydrocarbon group having 1 to 30 carbon atoms, wherein a part or all of hydrogen atoms included in the alicyclic hydrocarbon group and the heterocyclic group represented by $R^2$, and a part or all of hydrogen atoms included in the hydrocarbon group represented by $R^3$ are not substituted or substituted; $R^{41}$ represents —CO—, —COO—, —OCO—, —O—CO—O—, —NHCO—, —CONH—, —NH—CO—O—, —O—CO—NH—, —NH—, —S—, —SO—, —SO$_2$— or —SO$_2$—O—; $R^{42}$ represents —CO—, —COO—, —OCO—, —NHCO—, —CONH—, —NH—CO—O—, —SO— or —SO$_2$—; m is an integer of 1 or 2; and n is an integer of 0 or 1, wherein in a case where $R^3$, $R^{41}$ and $R^{42}$ are each present in a plurality of number, a plurality of $R^3$s, $R^{41}$s or $R^{42}$s are each independently as defined, and wherein a site denoted by * is a binding site with —O— in the formula (1).

2. The radiation-sensitive resin composition according to claim 1, wherein $M^+$ in the formula (1) represents a sulfonium cation or an iodonium cation.

3. The radiation-sensitive resin composition according to claim 1, wherein the base polymer includes a structural unit represented by a formula (2):

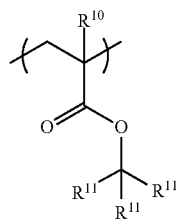

wherein, in the formula (2), $R^{10}$ represents a hydrogen atom or a methyl group; and $R^{11}$s each independently represent a linear or branched alkyl group having 1 to 4 carbon atoms or an alicyclic group having 4 to 20 carbon atoms, or two of $R^{11}$s taken together represent an alicyclic group having 4 to 20 carbon atoms together with the carbon atom to which the two of $R^{11}$s bond and $R^{11}$ other than the two of $R^{11}$s represents a linear or branched alkyl group having 1 to 4 carbon atoms or an alicyclic group having 4 to 20 carbon atoms.

4. The radiation-sensitive resin composition according to claim 1, wherein $R^2$ represents a substituted or unsubstituted cyclohexyl group or a substituted or unsubstituted adamantyl group.

5. The radiation-sensitive resin composition according to claim 1, wherein $R^2$ represents a group comprising a lactone structure.

6. The radiation-sensitive resin composition according to claim 1, further comprising an alkali-soluble polymer.

7. The radiation-sensitive resin composition according to claim 6, further comprising a crosslinking agent capable of crosslinking the alkali-soluble polymer in a presence of an acid.

8. The radiation-sensitive resin composition according to claim 1, further comprising a polymer which comprises a fluorine atom.

9. The radiation-sensitive resin composition according to claim 8, further comprising a lactone compound.

10. A radiation-sensitive acid generating agent comprising a compound represented by a formula (1):

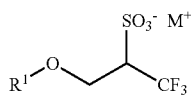

wherein, in the formula (1), $R^1$ is a group represented by a formula (a1); and $M^+$ represents a radiation-degradable monovalent cation,

wherein, in the formula (a1), $R^2$ represents an alicyclic hydrocarbon group having 3 to 30 carbon atoms or a heterocyclic group having 3 to 30 ring atoms; $R^3$ represents a divalent hydrocarbon group having 1 to 30 carbon atoms, wherein a part or all of hydrogen atoms included in the alicyclic hydrocarbon group and the heterocyclic group represented by $R^2$, and a part or all of hydrogen atoms included in the hydrocarbon group represented by $R^3$ are not substituted or substituted; $R^{41}$ represents —CO—, —COO—, —OCO—, —O—CO—O—, —NHCO—, —CONH—, —NH—CO—O—, —O—CO—NH—, —NH—, —S—, —SO—, —SO$_2$— or —SO$_2$—O—; $R^{42}$ represents —CO—, —COO—, —OCO—, —NHCO—, —CONH—, —NH—CO—O—, —SO— or —SO$_2$—; m is an integer of 1 or 2; and n is an integer of 0 or 1, wherein in a case where $R^3$, $R^{41}$ and $R^{42}$ are each present in a plurality of number, a plurality of $R^3$s, $R^{41}$s or $R^{42}$s are each independently as defined, and wherein a site denoted by * is a binding site with —O— in the formula (1).

11. The radiation-sensitive acid generating agent according to claim 10, wherein $M^+$ in the formula (1) represents a sulfonium cation or an iodonium cation.

12. The radiation-sensitive acid generating agent according to claim 10, wherein $R^2$ represents a substituted or unsubstituted cyclohexyl group or a substituted or unsubstituted adamantyl group.

13. The radiation-sensitive acid generating agent according to claim 10, wherein $R^2$ represents a group comprising a lactone structure.

* * * * *